(12) United States Patent
Schwammenthal et al.

(10) Patent No.: US 7,201,772 B2
(45) Date of Patent: Apr. 10, 2007

(54) FLUID FLOW PROSTHETIC DEVICE

(75) Inventors: Ehud Schwammenthal, Raanana (IL); Yosi Tuval, Netanya (IL); Raphael Benary, Tel-Aviv (IL)

(73) Assignee: Ventor Technologies, Ltd., Raanana (IL)

( * ) Notice: Subject to any disclaimer, the term of this patent is extended or adjusted under 35 U.S.C. 154(b) by 0 days.

(21) Appl. No.: 11/024,908

(22) Filed: Dec. 30, 2004

(65) Prior Publication Data

US 2006/0149360 A1 Jul. 6, 2006

Related U.S. Application Data

(63) Continuation-in-part of application No. PCT/IL2004/00601, filed on Jul. 6, 2004.

(60) Provisional application No. 60/485,156, filed on Jul. 8, 2003.

(51) Int. Cl.
*A61F 2/06* (2006.01)
*A61F 2/24* (2006.01)

(52) U.S. Cl. .................. 623/2.18; 623/2.19; 623/2.12; 623/1.26; 623/1.24

(58) Field of Classification Search ............ 623/1.24, 623/1.25, 1.26, 2.12, 2.13, 2.14, 2.15, 2.16, 623/2.17, 2.18, 2.19
See application file for complete search history.

(56) References Cited

U.S. PATENT DOCUMENTS

| 4,078,268 | A | 3/1978 | Possis |
| 4,491,986 | A | 1/1985 | Gabbay |
| 4,846,830 | A | 7/1989 | Knoch et al. |
| 5,108,425 | A | 4/1992 | Hwang |
| 5,178,632 | A | 1/1993 | Hanson |
| 5,332,402 | A | 7/1994 | Teitelbaum |
| 5,344,442 | A | 9/1994 | Deac |
| 5,354,330 | A | 10/1994 | Hanson et al. |
| 5,411,552 | A | 5/1995 | Andersen et al. |
| 5,840,081 | A | 11/1998 | Andersen et al. |
| 5,908,451 | A | 6/1999 | Yeo |
| 5,908,452 | A | 6/1999 | Bokros et al. |
| 5,964,405 | A | 10/1999 | Benary et al. |
| 6,076,742 | A | 6/2000 | Benary |
| 6,091,042 | A | 7/2000 | Benary |
| 6,168,614 | B1 | 1/2001 | Andersen et al. |

(Continued)

FOREIGN PATENT DOCUMENTS

WO    WO 05/002466    1/2005

OTHER PUBLICATIONS

U.S. Appl. No. 60/530,781.

(Continued)

*Primary Examiner*—Corrine McDermott
*Assistant Examiner*—Thomas J. Sweet
(74) *Attorney, Agent, or Firm*—Ladas and Parry LLP

(57) ABSTRACT

A prosthetic device including a valve-orifice attachment member attachable to a valve in a blood vessel and including a fluid inlet, and a diverging member that extends from the fluid inlet, the diverging member including a proximal end near the fluid inlet and a distal end distanced from the proximal end, wherein a distal portion of the diverging member has a larger cross-sectional area for fluid flow therethrough than a proximal portion thereof. The diverging member may have a diverging taper that causes fluid to flow therethrough with pressure recovery at the distal end thereof.

16 Claims, 16 Drawing Sheets

U.S. PATENT DOCUMENTS

| | | | |
|---|---|---|---|
| 6,287,339 B1 | 9/2001 | Vazquez et al. | |
| 6,312,465 B1 | 11/2001 | Griffin | |
| 6,454,799 B1 | 9/2002 | Schreck | |
| 6,458,153 B1 | 10/2002 | Bailey et al. | |
| 6,652,578 B2 | 11/2003 | Bailey et al. | |
| 6,682,559 B2* | 1/2004 | Myers et al. | 623/2.13 |
| 6,830,584 B1 | 12/2004 | Seguin | |
| 6,875,231 B2 | 4/2005 | Anduiza et al. | |
| 6,908,481 B2 | 6/2005 | Cribier | |
| 7,018,406 B2 | 3/2006 | Seguin et al. | |
| 7,018,408 B2 | 3/2006 | Bailey | |
| 2002/0026233 A1* | 2/2002 | Shaknovich | 623/1.24 |
| 2002/0186558 A1 | 12/2002 | Plank et al. | |
| 2003/0023300 A1 | 1/2003 | Bailey et al. | |
| 2003/0130727 A1* | 7/2003 | Drasler et al. | 623/1.24 |
| 2003/0130729 A1 | 7/2003 | Paniagua et al. | |
| 2003/0171805 A1 | 9/2003 | Berg | |
| 2004/0044402 A1* | 3/2004 | Jung et al. | 623/1.24 |
| 2004/0059429 A1 | 3/2004 | Amin et al. | |
| 2004/0106976 A1 | 6/2004 | Bailey et al. | |
| 2004/0186563 A1 | 9/2004 | Lobbi | |
| 2004/0210304 A1 | 10/2004 | Sequin et al. | |
| 2004/0260389 A1* | 12/2004 | Case et al. | 623/1.24 |
| 2005/0075720 A1 | 4/2005 | Nguyen et al. | |
| 2005/0096734 A1* | 5/2005 | Majercak et al. | 623/1.24 |
| 2005/0137688 A1 | 6/2005 | Salahieh et al. | |
| 2005/0137690 A1 | 6/2005 | Salahieh et al. | |
| 2005/0137691 A1 | 6/2005 | Salahieh et al. | |
| 2005/0182483 A1* | 8/2005 | Osborne et al. | 623/1.24 |
| 2005/0197695 A1 | 9/2005 | Stacchino et al. | |
| 2005/0240200 A1 | 10/2005 | Bergheim | |
| 2006/0025855 A1 | 2/2006 | Lashinski et al. | |
| 2006/0025857 A1 | 2/2006 | Bergheim et al. | |
| 2006/0058872 A1 | 3/2006 | Salahieh et al. | |

OTHER PUBLICATIONS

U.S. Appl. No. 60/465,141.

Heinrich RS et al., Ann Biomed Eng. Nov.-Dec. 1996;24(6):685-94. Experimental analysis of fluid mechanical energy losses in aortic valve stenosis: importance of pressure recovery.

Marcus RH et al., Circulation. Sep. 1, 1998;98(9):866-72. Assessment of small-diameter aortic mechanical prostheses: physiological relevance of the Doppler gradient, utility of flow augmentation, and limitations of orifice area estimation.

PD Stein et al., Circulation Research, vol. 39, 5 8-65, 1976 by American Heart Association. Turbulent blood flow in the ascending aorta of humans with normal and diseased aortic valves.

Weyman AB et al., Rev Cardiovasc Med. 2005;61(1)23-32. Aortic Stenosis: Physics and Physiology-What Do the Numbers Really Mean?.

Deac RF et al., Ann Thorac Surg. Aug. 1995;60(2 Suppl):S433-8. New evolution in mitral physiology and surgery: mitral stentless pericardial valve.

Heinrich RS et al., J Heart Valve Dis. Sep. 1999;8(5):509-15. Valve orifice area alone is an insufficient index of aortic stenosis severity: effects of the proximal and distal geometry on transaortic energy loss, an abstract.

* cited by examiner

FLUID FLOW PROSTHETIC DEVICE

CROSS REFERENCE TO OTHER APPLICATIONS

This application is a continuation-in-part of copending PCT Patent Application PCT/IL2004/000601, filed Jul. 6, 2004, claiming priority from U.S. Provisional Patent Application 60/485,156, filed Jul. 8, 2003, the disclosures of which are incorporated herein by reference.

FIELD OF THE INVENTION

The present invention relates to implantable prosthetic devices. The invention is particularly useful in prosthetic devices implantable by transarterial delivery for the treatment of aortic stenosis in the aortic valve of a patient's heart, and the invention is therefore described below with respect to such application. It will be appreciated, however, that the invention could also be used for other treatments, such as but not limited to, aortic regurgitation, mixed aortic stenosis and regurgitation, other valvular lesions, or the treatment of obstructed blood vessels or other body passageways, such as the urinary tract or gastrointestinal tract. The invention also relates to methods for implanting such prosthetic devices.

BACKGROUND OF THE INVENTION

Aortic stenosis is the obstruction of outflow from the left ventricular chamber into the aorta caused by a restricted opening of the aortic valve during left ventricular contraction and ejection. The diminished aortic valve opening area (from normally more than 3 $cm^2$ in an averaged sized adult to less than 0.5 $cm^2$ in severe cases) results in a significant pressure drop across the valve, and normal cardiac output and aortic pressure can only be maintained at the expense of an increased left ventricular systolic pressure. The high intracavitary pressure which has to be generated by the left ventricular chamber results in increased wall tension and myocardial oxygen demand. Adaptive processes such as hypertrophy (compensatory increase in muscle mass) allow the heart to withstand this increased pressure load for some time, but ultimately, pump failure is inevitable.

In the majority of cases (and in more than 90% of all patients older than 65 years) aortic stenosis is caused by progressive fibrous and calcified degeneration of an originally normal valve, a process which is favored by hyperlipoproteinemia, arterial hypertension, and aging (acquired calcified aortic stenosis). The average survival of a patient with severe aortic stenosis and shortness of breath is less than two years. Since death may occur suddenly in a substantial portion of cases, some investigators recommend preventive surgery even in asymptomatic patients, provided they are good surgical candidates.

Surgical results in the selected group of patients with isolated aortic stenosis are reasonable. Operative mortality in such patients is about 5%. However, most individuals with significant aortic stenosis are in their seventies and eighties. These patients have usually multiple comorbid risk factors, such as coronary artery disease, cerebrovascular disease, generalized atherosclerosis, renal failure, or diabetes. Consequently, surgical mortality and morbidity are substantial. Moreover, if the calcified aortic valve is replaced by a mechanical prosthesis, anticoagulation is mandatory to reduce thromboembolic complications, which exposes the patient to an increased risk of serious bleeding, particularly with increasing age. Implantation of biological prostheses is therefore usually preferred in the elderly, but surgically implanted biological valves may have a suboptimal hemodynamic profile, because the suture ring on which the valve needs to be mounted reduces the space available for the valve itself. This poses a particular problem in women, where bioprostheses of a smaller size (which have to be used because of the smaller cardiac dimensions) may result in significant residual outflow obstruction.

Because of the significant risk of elderly patients undergoing open-heart surgery on cardiopulmonary bypass, which includes death, disabling stroke, respiratory and renal complications, dilatation of the narrowed valve using balloon-catheters was hoped to provide an alternative to surgery. Unfortunately, because immediate results of the balloon dilatation are suboptimal, and recoil of the stenosis reoccurs within weeks and months in virtually all patients, outcome is as poor as in patients who do not undergo surgery. Balloon-dilatation is therefore considered only justified in patients with a clear contraindication to surgery or—in rare cases—as a "bridging procedure".

Recently, in analogy to the use of stents in coronary arteries, it has been proposed to use valved stents in order to achieve a sufficiently large valve area and avoid elastic recoil and restenosis. Spencer et al (U.S. Pat. No. 6,730,118), Andersen et al (U.S. Pat. No. 5,840,081) and Gabbay (U.S. Pat. No. 4,759,758) all describe a valved stent of certain designs that are intended for transarterial deployment. Cribier et al describes, in WO 98/29057, a collapsible stent which has a valve attached to it by circumferential suturing. The mesh/valve system is deployed via an inflatable balloon. In 1992, Andersen et al. reported their experience with a foldable porcine aortic valve sutured in an expandable stainless-steel stent. The valved stent was mounted on an 18–22 mm balloon-catheter front-loaded in a 16F Mullins long sheath and implanted in the pulmonary position, completely displacing the pulmonary cusps (or leaflets), which were pressed between stent and pulmonary artery wall with full deployment of the stent. However, this approach could result in coronary artery occlusion when undertaken in the aortic position, which would be fatal to the patient.

Even when the stent is not deployed across the full area of the aortic annulus, atheromatous deposits on the ventricular side of the aortic cusps (or leaflets) may be pushed against the ostia of the coronary arteries causing severe coronary obstruction or embolization. Severe distention of a heavily calcified aortic valve to allow deployment of a sizeable stent may also cause embolization of calcium deposits from the valve or a tear in the valve resulting in significant aortic regurgitation. Furthermore, a large stent-valve may also interfere with surrounding structures such as the anterior mitral leaflet (causing damage to it or impairing its function), and if protruding into the left ventricular outflow tract, the basal ventricular septum, which is usually hypertrophied in significant aortic stenosis.

BRIEF SUMMARY

The present invention seeks to provide a prosthetic device attachable to an existing valve of a blood vessel, and capable of recovering fluid pressure of flow through the valve and the prosthetic device, as is described more in detail hereinbelow.

There is provided in accordance with an embodiment of the present invention a prosthetic device including a valve-orifice attachment member attachable to a valve in a blood vessel and including a fluid inlet, and a diverging member that extends from the fluid inlet, the diverging member including a proximal end near the fluid inlet and a distal end distanced from the proximal end, wherein a distal portion of the diverging member has a larger cross-sectional area for fluid flow therethrough than a proximal portion thereof. The diverging member may have a diverging taper that causes fluid to flow therethrough with pressure recovery at the distal end thereof. For example, the taper may widen with a widening angle α from 1° to 25° (e.g., about 5°). The fluid inlet may be non-divergent in (the distal direction (e.g., convergent or straight).

An inner envelope may line an inner surface of at least one of the diverging member and the valve-orifice attachment member. The inner envelope may be continuous or may have discontinuities (e.g., openings or slits).

The valve-orifice attachment member may include clasping members adapted to clasp opposite sides of the valve near the orifice, for example, an annular clamp adapted to engage valve leaflets.

In accordance with an embodiment of the present invention a prosthetic valve may be disposed in the diverging member, the prosthetic valve being adapted to control fluid flow through the diverging member (such as, but not limited to, a mechanical heart valve, biological heart valve, a heart valve allograft, a vein valve, and/or a pericardial valve). A prosthetic valve may alternatively or additionally be disposed in the fluid inlet section.

Further in accordance with an embodiment of the present invention an annular array of bracing elements may be at the distal end of the diverging member engageable with an inner surface of a blood vessel. A plurality of axially-extending struts may be pivotally mounted near the valve-orifice attachment member and extend through at least a portion of the diverging member.

Further features and advantages of the invention will be apparent from the description below.

BRIEF DESCRIPTION OF THE DRAWINGS

The invention is herein described, by way of example only, with reference to the accompanying drawings, wherein:

FIGS. 11A–11C illustrate the same kind of prosthetic device with bracing elements as shown in FIGS. 9–11, wherein FIG. 11A illustrates the prosthetic device attached to valve leaflets. FIG. 11B illustrates blood flow through the prosthetic device during systole, and FIG. 11C illustrates blood flow through the prosthetic device during diastole;

DESCRIPTION OF EMBODIMENTS

Figure 1A:
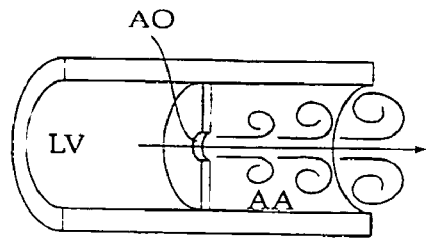
FIGS. 1A, 1B and 1C are diagrams helpful in explaining the health problem caused by a stenotic valve and the advantages of replacing a stenotic valve orifice by a prosthetic device constructed in accordance with the present invention.
Figure 1B:
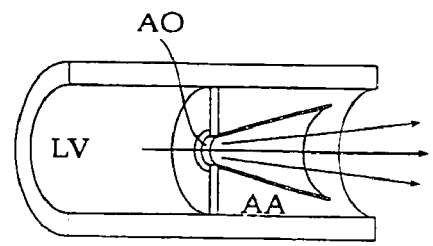
Figure 1C:
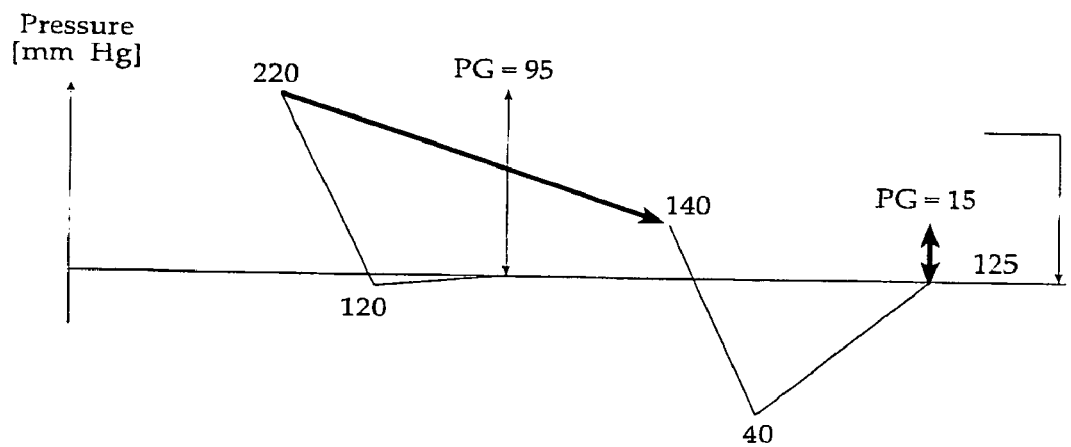
Figure 2:
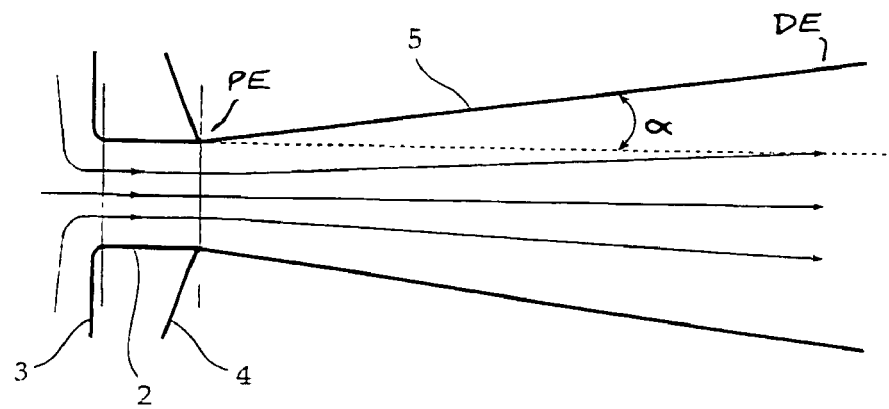
FIG. 2 is a diagram illustrating a prosthetic device constructed in accordance with the present invention to treat the above health problem by producing non-turbulent blood flow into the aorta with pressure recovery.

Reference is now made to FIG. 2, which diagrammatically illustrates one non-limiting construction of a prosthetic device in accordance with the present invention, and FIGS. 1A–1C, which diagrammatically illustrate the manner in which such a prosthetic device may be used for alleviating the work load placed on the heart by an aortic valve suffering from significant aortic stenosis. It is noted that the present invention is not dependent upon any theory or explanation of the manner in which the blood flows in the circulatory system, and any explanation or theory is provided simply for the purposes of elucidation. It is also noted that the embodiments described in detail hereinbelow are only exemplary and the invention is not limited to these specific constructions.

The principles of flow regulation in the cardiovascular system may be similar to those in pipeline systems. Aortic pressure and cardiac output are regulated by the baroreceptor-system with its stretch-receptors in the aorta and proximal aortic artery branches (innominate and carotid arteries). Any loss of pressure may lead to a centrally mediated increase in cardiac output until the preset systemic pressure is again reached.

FIG. 1A diagrammatically illustrates how blood flows from the left ventricule (LV) through the aortic orifice (AO) into the aorta artery (AA). The flow may be affected by a stenotic condition in the aortic orifice AO. Such a stenotic condition effectively reduces the size of the aortic orifice AO to produce a turbulent flow into the aortic artery AA, which produces a substantial loss in pressure of the blood entering the aortic artery. Such pressure loss is sensed by the baroreceptor system which acts to increase the left ventricular systolic intracavitary pressure, thereby producing increased wall tension in the ventricular chamber, increased myocardial oxygen demand, and ultimately heart failure.

As shown in FIG. 1B, when a stenotic valve orifice, as shown in FIG. 1A, is replaced by a prosthetic device of the same throat size but including a Venturi tube configuration, namely one having (in the chosen example) a diverging conical configuration, there is produced a non-turbulent blood flow into the aorta with pressure recovery at the distal (wide) end of the device. The baroreceptor system may therefore not sense a loss of pressure, and may therefore not increase the left ventricular workload in order to compensate for such pressure loss. Accordingly, the replacement of a stenotic valve as shown in FIG. 1A, by a prosthetic device with a diverging (preferably conical) configuration as shown in FIG. 1B, may reduce the workload placed on the left ventricular chamber.

FIG. 1C diagrammatically illustrates the difference in the heart load when acting against a stenotic valve as shown in FIG. 1A, and when such a valve is replaced by a prosthetic device having the diverging conical configuration as shown in FIG. 1B. For purposes of example, the diagram of FIG. 1C is based on the following conditions: cardiac output is 5 l/min: the cross-sectional area of the throat is 0.5 cm$^2$; the required pressure gradient is 100 mmHg; and the aortic pressure demanded by the baroreceptors-system in the given example is 125. Thus, the substantial decrease in pressure head loss produced in the stenotic valve (FIG. 1A) may cause the blood pressure in the left ventricle to be 220 mm Hg in systole. However, the addition of a prosthetic device with the same critical area having the diverging conical configuration of FIG. 1B may provide a pressure recovery of 85 mm Hg, and may produce a blood pressure of 140 mm Hg in systole. In essence, pressure head loss may be reduced from 95 to 15 mm Hg.

The prosthetic device diagrammatically illustrated in FIG. 2 may include an annular base 2 (also referred to as base section 2 or throat section 2) having a circular cross-section to be implanted in the aortic orifice AO; an annular clamp 3 at its outer end engageable with one face of the valve leaflets (cusps) in the ventricular chamber, and acting as a barrier against regurgitation; and another annular clamp 4 engageable with the opposite face of the valve leaflets. In this and all other embodiments of the invention, all components of the prosthetic device may be constructed of any suitable medically safe material of combination of such materials, such as but not limited to, metal (e.g., stainless steel, NITINOL and others), or plastic (e.g., nylon, polyurethane and others).

The base section 2 of the prosthetic device may be relatively short, straight, of uniform diameter, and may be located within the aortic orifice. The remainder of the prosthetic device may extend into the aorta artery AA and may be of a diverging (preferably conical) configuration, as shown at 5, in which its diameter gradually increases from its proximal end PE within the heart left ventricle, to its distal end DE within the aorta. The angle of the taper ($\alpha$) of the diverging (preferably conical) section 5 may be determined according to fluid dynamic principles of Venturi flow, such as to produce a non-turbulent blood flow into the aorta, with gradually decreasing velocity and with pressure recovery at the distal end of the prosthetic device.

The diverging section 5 may be straight or curved in any way, concavely or convexly, e.g., parabolic, tulip-shaped, bugle-shaped or otherwise. The distal end of diverging section 5 has a larger cross-sectional area for fluid flow therethrough than the proximal end.

Thus, as is well known in fluid dynamics, the flow velocity increases through the small diameter of the base or throat section 2, thereby decreasing the static or lateral pressure; whereas the gradual expansion of the diverging (preferably conical) section 5 decreases the flow velocity, thereby regaining the static or lateral pressure (pressure recovery). Such a construction produces a laminar or non-turbulent flow, reducing or eliminating flow separation in the diverging (preferably conical) section 5, and thereby decreases head losses at the distal end DE of the prosthetic device. The described invention therefore represents a pressure-recovering device, but is not limited to this.

As will be described more particularly below, the prosthetic device may carry a prosthetic valve at its distal end DE. Several commercial prosthetic aortic valve systems are currently available, generally classified as mechanical heart valves and biological heart valves, respectively (either heart valve allografts, vein valves, or pericardial valves).

Figure 3:
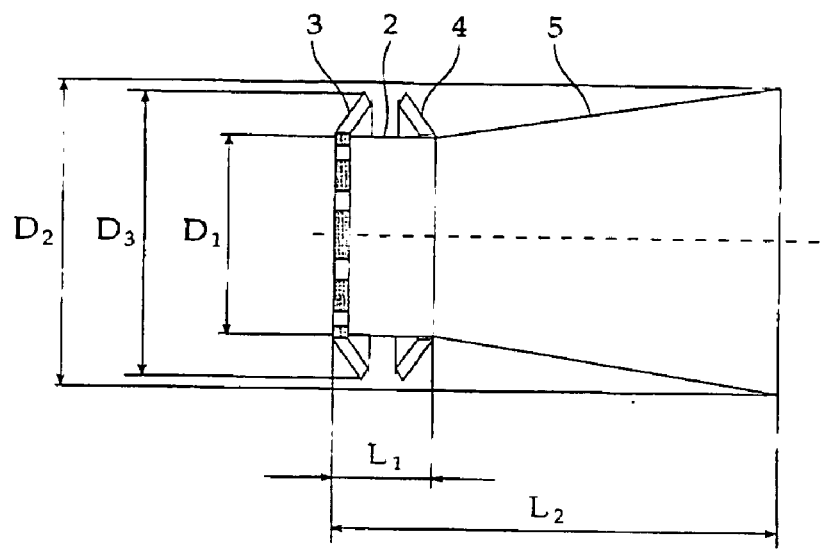
FIG. 3 is a side view of a prosthetic device constructed in accordance with FIG. 2.
Figure 4:
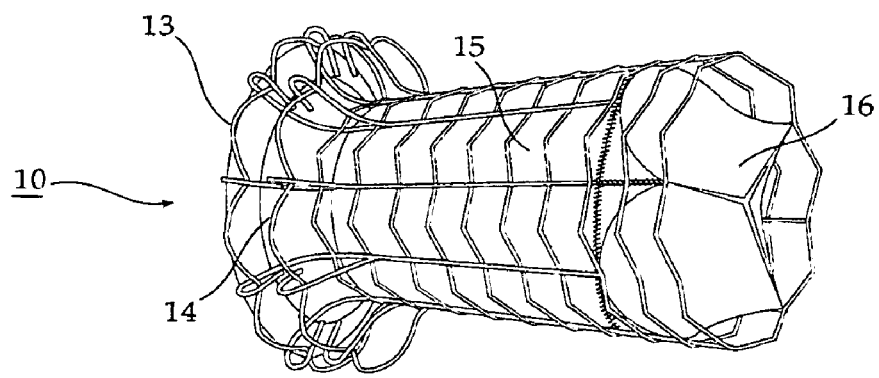
FIG. 4 is a simplified pictorial illustration of a prosthetic device, constructed and operative in accordance with another embodiment of the present invention.

In order to accommodate patients of different sizes and weights, the prosthetic device, in its expanded state, may have the following dimensions as shown in FIG. 3: the diameter $D_1$ at the proximal end PE may be within the range of 5–30 mm and typically approximately 14 mm; the diameter $D_2$ at the distal end DE may be 10–40 mm and typically approximately 20 mm; the axial length of $L_1$ of the base or throat section 2 may be 0–20 mm and typically approximately 2 mm; and the axial length $L_2$ from the proximal end to the distal end may be 5–70 mm and typically approximately 37 mm.

In another non-limiting example, a typical diameter $D_1$ of the throat section 2 may be 13–15 mm (covering approximately ⅔ of the average outflow tract diameter of an adult); a typical length $L_1$ may be 5 mm; a typical length ($L_2$-$L_1$) of the diverging conical section 5 may be 18 to 60 mm; and a typical angle $\alpha$ (widening angle, deviation from straight segment, that is, half-cone angle) may be from 0.1° to 50°, typically approximately 5–8°, wherein an angle $\alpha$ of 5° produces almost full pressure recovery for laminar flow. For example, if the straight throat section 2 has a diameter of 14 mm (cross-sectional area 154 mm$^2$), then a tube attached to this segment and widening with an angle $\alpha$ of 5° over a distance of 35 mm may have a diameter of 20 mm at its distal end (cross-sectional area 314 mm$^2$). Consequently, this device may be able to accommodate a 20 mm biological prosthesis at its end (in the aorta) with favorable hemodynamic properties, although the throat size (straight segment within the valve) is only 14 mm in diameter.

The Prosthetic Device of FIGS. 4–8

As indicated earlier, a prosthetic device constructed in accordance with the present invention preferably also includes at the distal end DE of the diverging preferably conical section 5, a prosthetic valve to be implanted with the prosthetic device. It is anticipated, however, that for some applications the prosthetic device may be implanted without a prosthetic valve, and the prosthetic valve implanted in a second subsequent operation in the aorta downstream of the prosthetic device.

FIGS. 4–8 illustrate a prosthetic device construction of a non-limiting embodiment of the present invention that includes a prosthetic valve.

Figure 5:
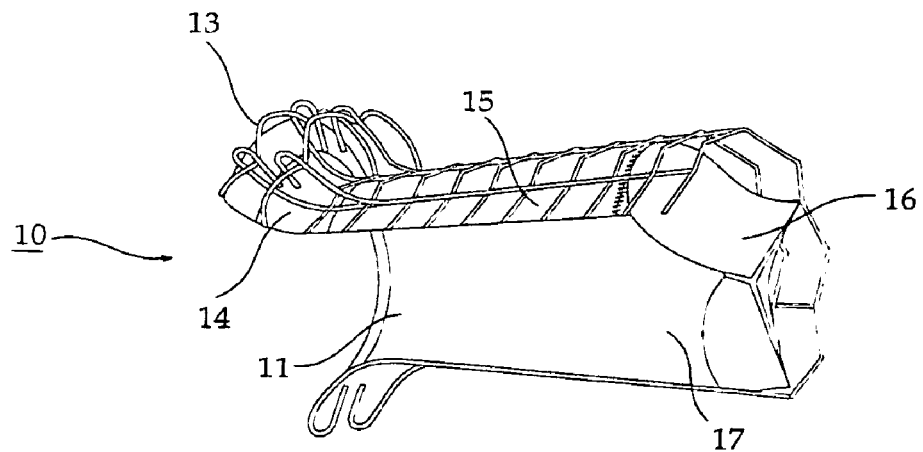
FIG. 5 a side view of the prosthetic device of FIG. 4.

As shown particularly in the sectional view of FIG. 5, the illustrated prosthetic device includes an expandable body 10 (e.g., constructed of a metal mesh) so as to be transarterially deliverable via a catheter to the implantation site, in this case, the aortic annulus or orifice of an aortic valve affected by aortic stenosis. The illustrated prosthetic device further includes an inner envelope 11, constructed, for example, without limitation, of a biological or flexible polymeric or other biocompatible material, lining the complete inner surface of body 10.

Body 10 and its liner 11 of the illustrated prosthetic device may include a short, straight throat section 12 constructed so as to be implanted in the aortic orifice (AO, FIG. 2). The prosthetic device may further include an annular clamp 13 to engage the face of the valve leaflets (cusps) on one side of the aortic orifice; an annular clamp 14 to engage the face of the valve leaflets on the opposite side of the aortic orifice (in one embodiment only a proximal annular clamp is used); and a diverging (preferably conical) section 15 extending into the aorta artery AA. The construction is such that the diverging (preferably conical) section 15 gradually increases in diameter from the short throat section 12 at the proximal end PE of the prosthetic device to its distal end DE, in order to produce a non-turbulent blood flow through the prosthetic device into the aorta, with pressure recovery at the distal end, as described above with respect to the embodiment of FIG. 2.

It is noted that in one embodiment of the invention, only a proximal annular clamp may be used. Fixation of the device at its distal end may be effected by an aortic wall stent, preferably, but not exclusively, self-expanding.

The distal end of the illustrated prosthetic device may include a prosthetic valve 16. Prosthetic valve 16 may be placed anywhere along the diverging section 15. Preferably, prosthetic valve 16 is a collapsible mechanical or biological valve (e.g. made of a pliable polymeric film) which is effective to open the distal end of the prosthetic device during systole, and to close it during diastole. For example, prosthetic valve 16 may be made of the same material as liner 11 and attached thereto along a zone of attachment, as shown at 17 in FIG. 5.

While a collapsible biological prosthetic valve is preferred, other prosthetic valves systems could be used, such as a ball-cage, a disc-cage, a tilting disc, a bileaflet, a check-valve, etc. In one embodiment a mechanical or synthetic prosthetic valve can be used. Another prosthetic valve which may be used is a pericardial valve, such as the Mitroflow Aortic Pericardial Heart Valve, commercially available from CarboMedics (a Sorin Group company), which has a streamlined sewing cuff intended to optimize heart valve placement for increased blood flow area.

It is further noted that the prosthetic valve 16 may have a diverging shape (e.g., conical) so that the prosthetic valve 16 is the diverging section 15. In other words, there is no need for constructing a diverging section with an additional prosthetic valve therein, rather the prosthetic valve may be the diverging member itself.

Figure 6:
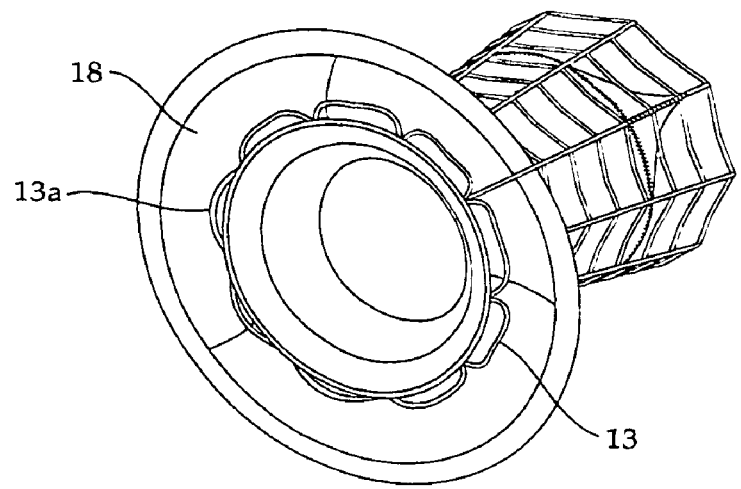
FIG. 6 is an end view from the heart side illustrating the prosthetic device of FIGS. 4 and 5 implanted in the aortic annulus.
Figure 7:
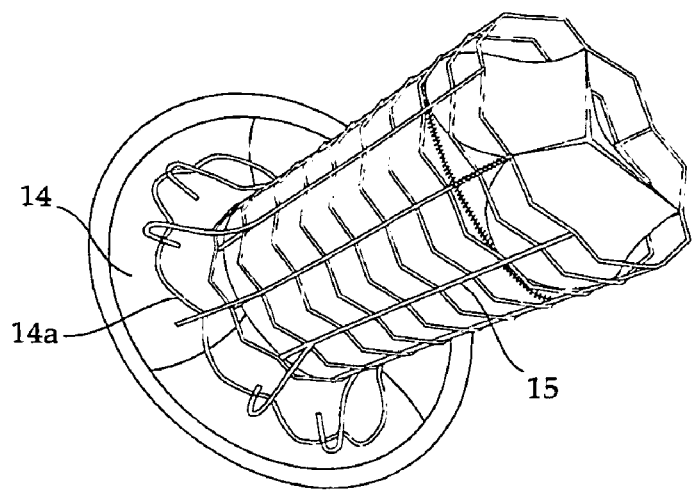
FIG. 7 is a perspective view from the aorta side of the implanted prosthetic device of FIGS. 4 and 5.
Figure 8:
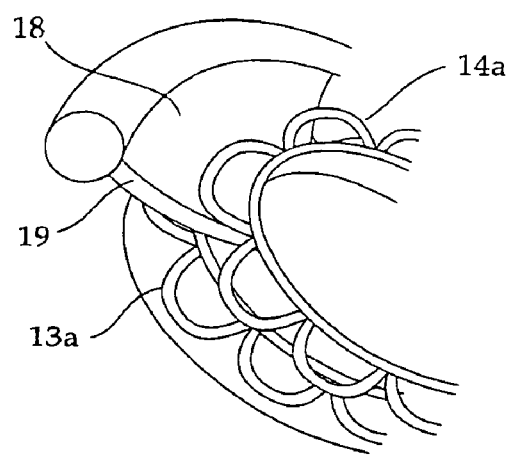
FIG. 8 is a fragmentary detail illustrating an example of the manner in which the annular clamps engage the opposite sides of the valve leaflets in the implanted condition of the prosthetic device.

In accordance with a non-limiting embodiment of the present invention, in the expanded condition of the illustrated prosthetic device, each of the annular clamps 13 and 14 may include an annular array of clasping members which engage the surfaces of the valve leaflets (cusps) on opposite sides of the aortic annulus, as illustrated more particularly in FIGS. 6–8. As illustrated particularly FIG. 8, annular clamp 13 may include an annular array of clasping members 13a engageable with surface 18 (FIG. 6) of the native valve leaflets at the heart left-ventricle side of the aortic annulus AO; and annular clamp 14 may include a similar annular array of clasping members 14a engageable with surface 19 (FIG. 8) of the native valve leaflets at the aorta side of the aortic annulus.

Any suitable method may be used for attaching the inner envelope or liner 11 to the inner surface of diverging section 10. Non-limiting examples include: adhesive bonding, e.g., by using a long-lasting biocompatible adhesive; ultrasonic welding, e.g., using sonic energy to soften the plastic envelope 11 where it contacts the diverging section 15; or injection-molding the polymeric material to embed the diverging section 15 therein. Other possible methods include a mechanical locking arrangement wherein the inner envelope is mechanically locked to the diverging section 15, or a suturing technique wherein the inner envelope is sutured to the diverging section 15.

As mentioned hereinabove, all components of the prosthetic device may be constructed of any suitable medically safe material of combination of such materials, such as but not limited to, metal (e.g., stainless steel, NITINOL and others), or plastic (e.g., nylon, polyurethane and others). Without limitation, liner 11 may be made of a suitable biocompatible polymeric or plastic material, or biological material (e.g. pericard).

Examples of metals that may be used are tungsten, platinum, and titanium. Metal alloys possessing the required physical properties include (but are not limited to) Stainless Steel 316 and NITINOL (nickel titanium), both of which are biocompatible and commercially available. For example NITINOL may be used for the annular clamps 13 and 14, and the diverging conical section 5, while another conventional metallic stent material, such as Stainless Steel 316, may be used for the base or throat section 12. Dacron is typically used for covering NITINOL-based devices, but other suitable biocompatible polymeric or elastomeric materials can be used for the inner envelope or liner 11.

Figure 9:
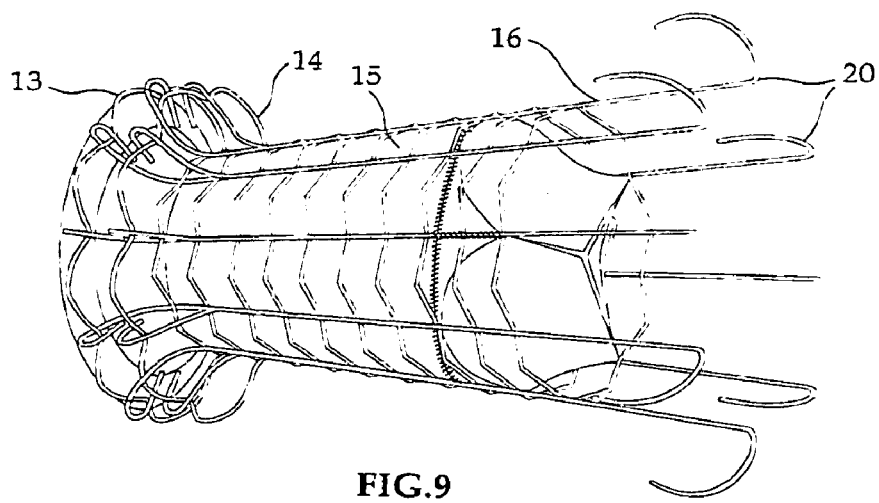
FIG. 9 illustrates a prosthetic device similar to that of FIG. 4 but including braces for bracing the distal end of the prosthetic device when implanted.
Figure 10:
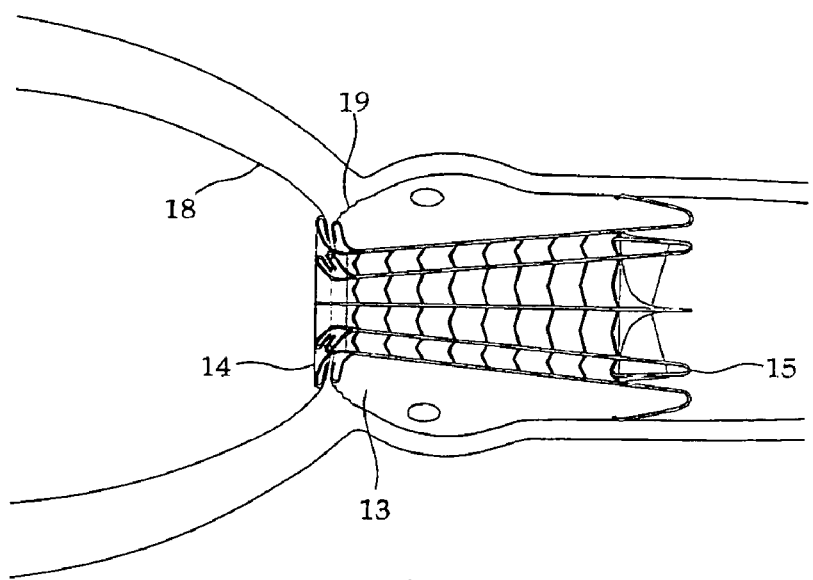
FIG. 10 illustrates the prosthetic device of FIG. 9 when implanted in the aortic annulus.
Figure 11:
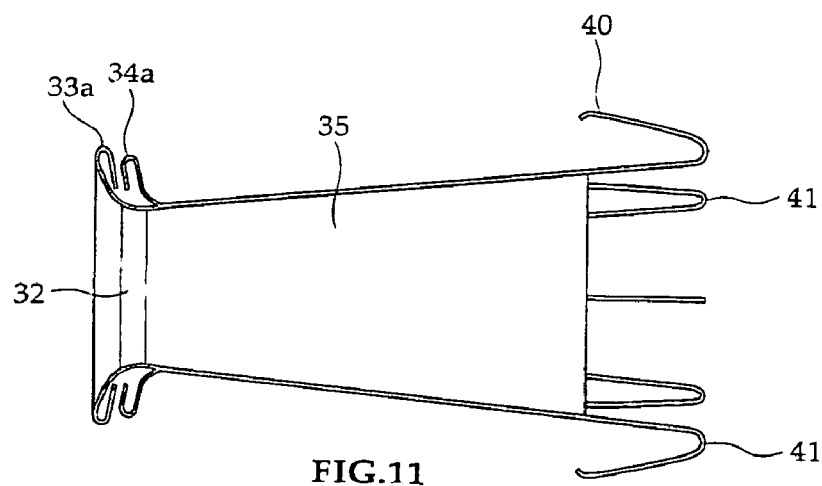
FIG. 11 illustrates a cross-section of another construction of a prosthetic device in accordance with the present invention.
Figure 11A:
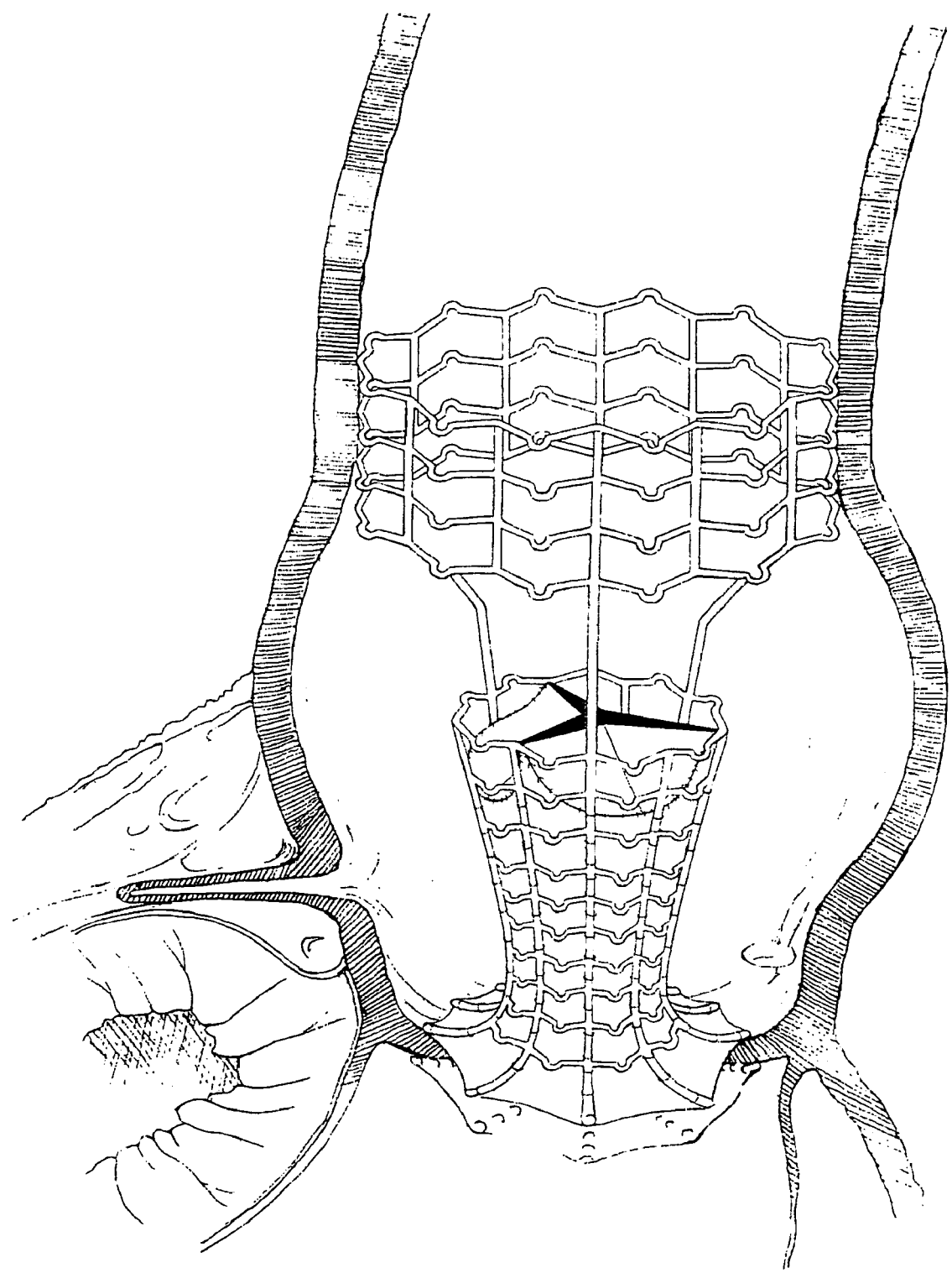
Figure 11B:
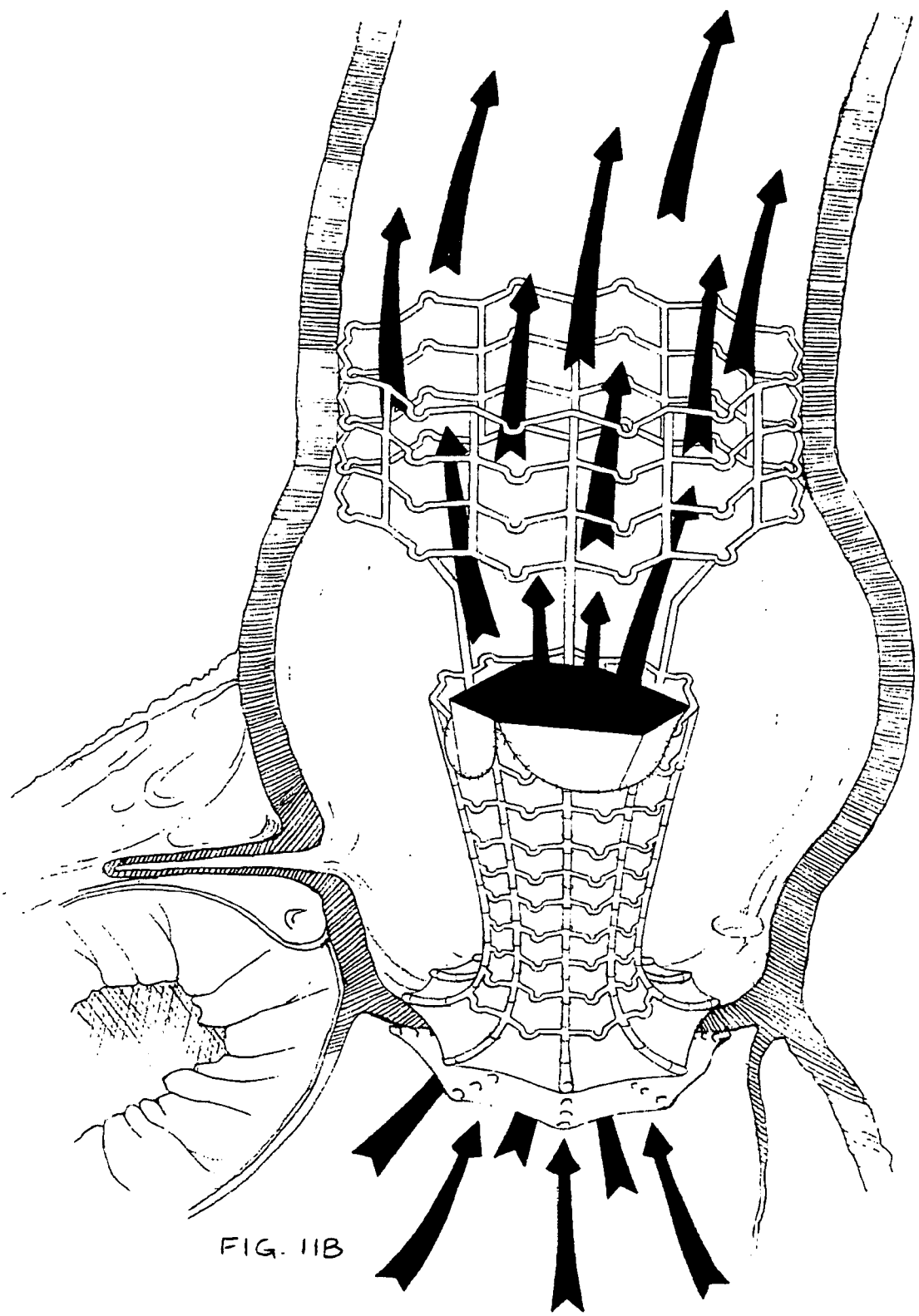
Figure 11C:
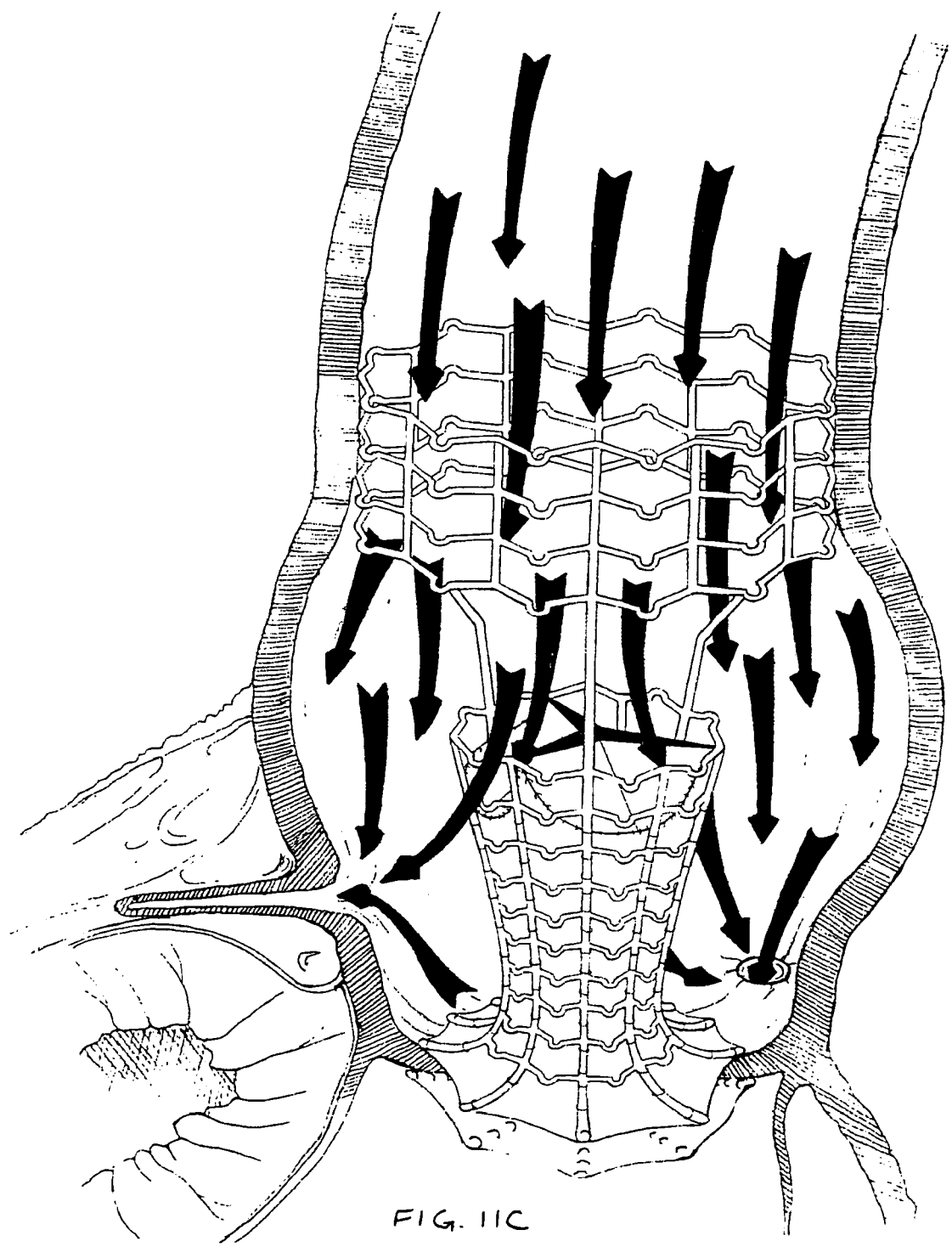

The Prosthetic Devices of FIGS. 9, 10 and FIG. 11 (and FIGS. 11A–11C)

FIG. 9 illustrates a prosthetic device similar to that described above with respect to FIGS. 4–8, and therefore to facilitate understanding, corresponding parts have been identified by the same reference numerals. The main difference in the prosthetic device illustrated in FIG. 9 is the provision of a plurality of bracing elements 20 carried by the distal end DE of the body 10 and engageable with the inner surface of the aorta for bracing the prosthetic device, particularly its distal end, within the aorta as shown in FIG. 10.

In FIG. 11, clasping members 34a of an annular clamp 34 may engage the distal (aorta) side of the valve leaflets in the aortic annulus. Bracing elements, generally designated 40, may comprise an annular array extending from the distal (broad) end of the prosthetic device, including connection elements 41. A diverging (preferably conical) section 35 extends from clasping members 34a to bracing elements 40. Clasping members 34a cooperate with clasping members 33a carried by a throat section 32 to clamp the device in the aortic orifice. Bracing elements 40 are configured so as to engage the inner surface of the aorta, preferably adjacent to, the distal end of the prosthetic device, in order to brace that end when the prosthetic device is implanted in the aortic annulus. They may be configured so as not to obstruct or occlude the coronary arteries adjacent to the aortic annulus (as described below with reference to FIG. 16F).

For simplification purposes, FIG. 11 omits the inner liner and the prosthetic valve, e.g. 11 and 16, respectively, shown in FIG. 5.

FIGS. 11A–11C illustrate the same kind of prosthetic device with bracing elements as shown in FIGS. 9–11. FIG. 11A illustrates the prosthetic device attached to valve leaflets (e.g., in the aortic annulus). FIG. 11B illustrates blood flow through the prosthetic device during systole. The blood flows through the diverging member of the prosthetic device in non-turbulent flow, and there is pressure recovery at the distal end of the diverging member. FIG. 11C illustrates blood flow through the prosthetic device during diastole. It is seen that the prosthetic device prevents the blood from flowing back through the valve orifice.

Figure 12:
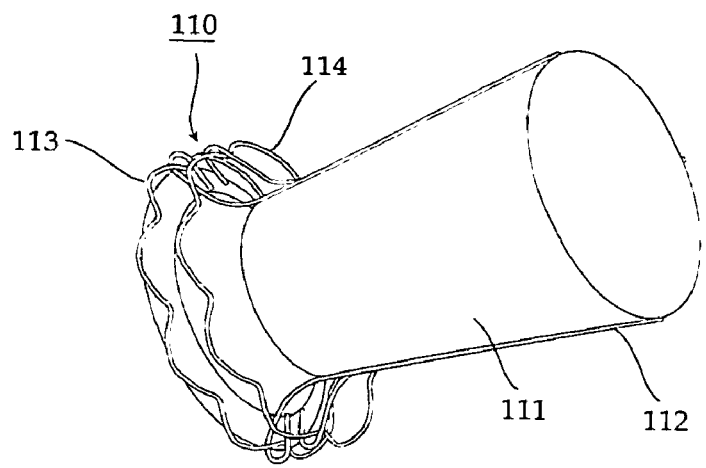
FIG. 12 is a simplified illustration of yet another prosthetic device constructed in accordance with the present invention.
Figure 13:
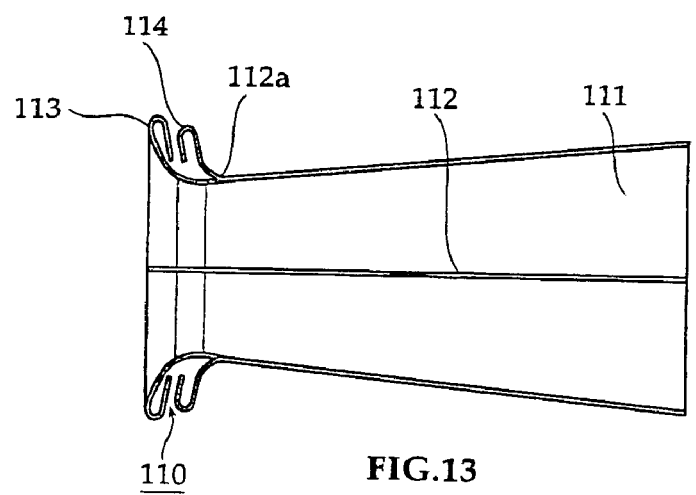
FIG. 13 is a side view of the device of FIG. 12.
Figure 14:
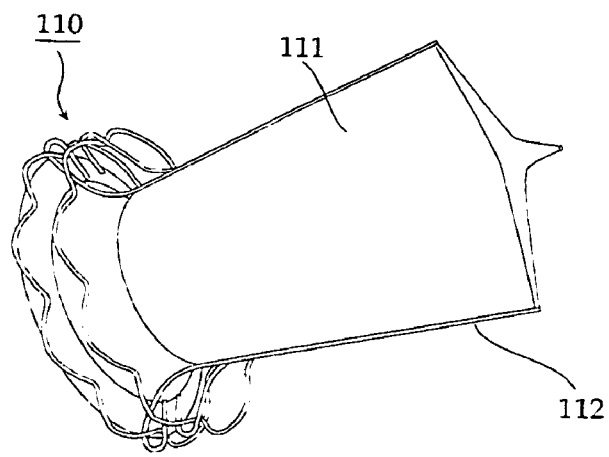
FIG. 14 illustrates the prosthetic device of FIGS. 12 and 13 in a mid-closed (not completely closed) condition.

The Prosthetic Device of FIGS. 12–14

FIGS. 12–14 illustrate a prosthetic device that may include a base 110 and an envelope 111, which may also serve as a prosthetic valve. During systole, the envelope 111 opens and assumes a diverging conical configuration so as to produce the non-turbulent blood flow into the aorta with pressure recovery at the distal end of the envelope; whereas during diastole, envelope 111 collapses to block the flow therethrough.

Base 110, which corresponds to the throat section (e.g., 12, FIG. 5) of the prosthetic device to be implanted into the aortic annulus, further includes two annular arrays of clasping members 113 and 114, on its opposite sides for engaging the opposite faces of the valve leaflets within the aortic annulus, which correspond to annular clamps 13, 14, of FIG. 5.

Envelope 111 lines the inner surface of base 110. It then extends outwardly of base 110 to define the diverging (preferably conical) section of the prosthetic device, and also a prosthetic valve carried by the distal end of the prosthetic device (corresponding to sections 15 and valve 16, respectively, in FIG. 5).

Envelope 111 may further include a plurality of axially-extending struts 112 pivotally mounted at 112a to base 110, to permit the envelope to expand, during systole, to its open-valve condition to permit blood therethrough, while at the same time assuming the diverging conical configuration for producing non-turbulent blood flow into the aorta with pressure recovery at the distal end. Struts 112 also permit envelope 111 to collapse during diastole in order to effectively block the blood flow therethrough, and thereby to perform the function of a prosthetic valve. FIG. 14 illustrates envelope 111 in a partially collapsed condition.

Reinforcing struts 112 may be constructed of the same material as base 110 and may be pivotally mounted to the base by integrally-formed hinges. Alternatively, reinforcing struts 112 may be of a different material, e.g., of a different metal or plastic, sufficiently stiff to support envelope 111 in its valve-open conical configuration during systole, and mechanically hinged to base 110 in any suitable manner.

It will thus be seen that the prosthetic device illustrated in FIGS. 12–14 not only acts to regulate the flow from the left ventricle into the aorta to produce the above-described non-turbulent flow into the aorta with pressure recovery, but also serves as a prosthetic valve which opens during systole and closes during diastole.

In the configuration shown in FIG. 13, as described above, the envelope 111 may open and close as a prosthetic valve. In other words, the diverging section of the prosthetic device may itself serve as the prosthetic valve that opens in systole and closes in diastole, without any need for placing a prosthetic valve somewhere in the diverging section (as shown and described in other embodiments).

Alternatively, instead of constructing the diverging section with the pivoting reinforcing struts 112, the diverging section may be the prosthetic valve itself, as described above with reference to the embodiment of FIGS. 4–8.

Modes of Deployment

As indicated above, the prosthetic device of the present invention may be implanted in an orifice formed in a wall of a body passageway. It is therefore constructed to have a compressed state for delivery via the body passageway to the implantation site and to be expandable at the implantation site to an expanded state for implantation into the orifice. The embodiments of the invention described above are intended for implantation in the aortic annulus of a patient's heart, and therefore are constructed for transarterial delivery to the aortic annulus and expansion at the aortic annulus for implantation therein.

A single-sheath mode of deployment is described below with respect to FIGS. 15A–15H and 16A–16h; and a two-sheath mode of deployment is described below with respect to FIGS. 17A–17h.

Single-Sheath Mode of Deployment

FIGS. 15A–15H diagrammatically illustrate a method of deploying the prosthetic device, e.g., of FIG. 2, using a single sheath; whereas FIGS. 16A–16F illustrate that method used for deploying a prosthetic device of the construction illustrated in FIG. 11, i.e., including an annular array of bracing elements 40.

In the single-sheath method illustrated in FIGS. 15A–15H, the prosthetic device, generally designated PD and of the construction illustrated in FIG. 2, is to be implanted into the aortic orifice AO of the aortic valve AV by means of the annular clamps 3, 4. When so implanted, the throat section 2 of the prosthetic device is implanted in the aortic orifice AO, and the diverging conical section 5 of the prosthetic device is received within the aortic artery AA.

In order to deliver the prosthetic device PD to the implantation site, it may be introduced into a catheter 200 which may include a balloon 201 and a sheath 202 for post implantation dilations. Balloon 201, in its deflated condition, receives the throat section 2 and the two annular clamps 3, 4 of the prosthetic device. Sheath 202 encloses the complete prosthetic device and retains it including its annular clamps 13, 14 and diverging conical section 15, in a compressed state for transarterial delivery. The device may also be introduced after performing balloon pre-dilation (balloon valvuloplasty), in which case the device insertion (implantation) catheter will not include a balloon.

Figure 15A:
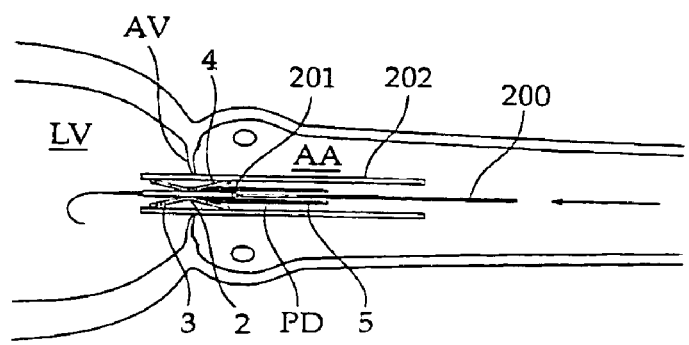
FIGS. 15A–15H and FIGS. 16A–16F illustrate a single-sheath method for implanting some types of prosthetic devices in accordance with the present invention.
Figure 15B:
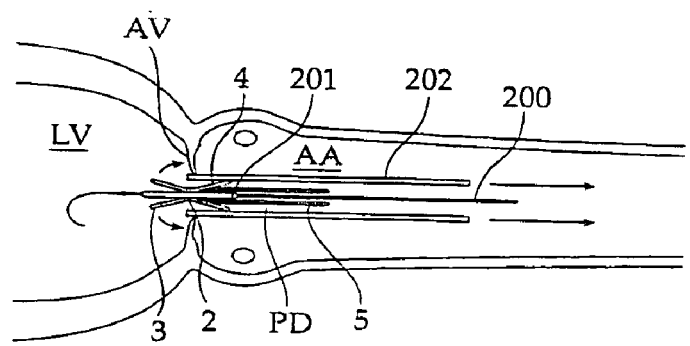
Figure 15C:
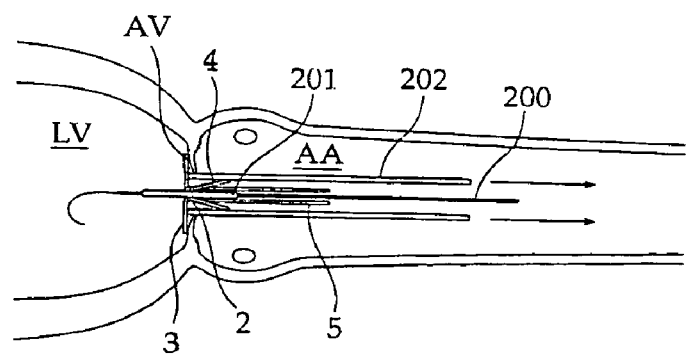
Figure 15D:
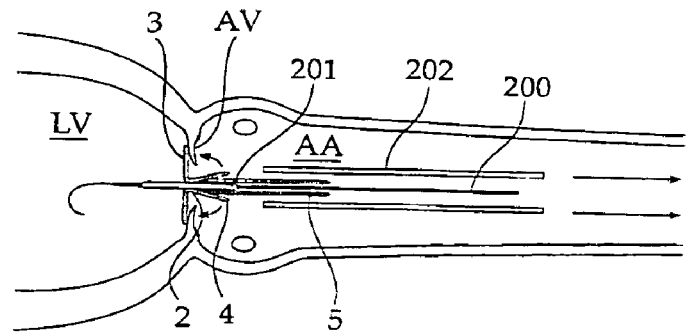
Figure 15E:
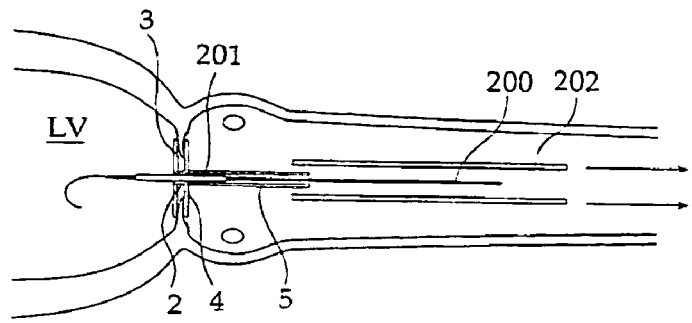

The catheter may be introduced into a peripheral artery of the patient and manipulated in a conventional manner to bring the throat section 2 into alignment with the aortic orifice AO, with the two annular clamps 3, 4, located on opposite sides of the valve leaflets defining the orifice (FIG. 15A).

Figure 15F:
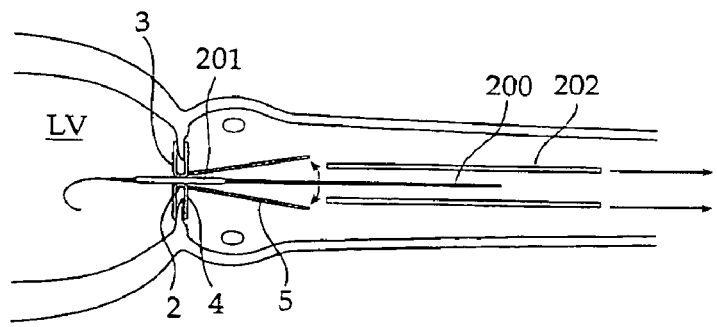
Figure 15G:
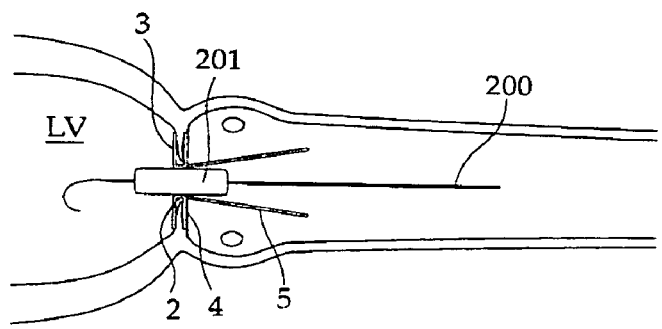
Figure 15H:
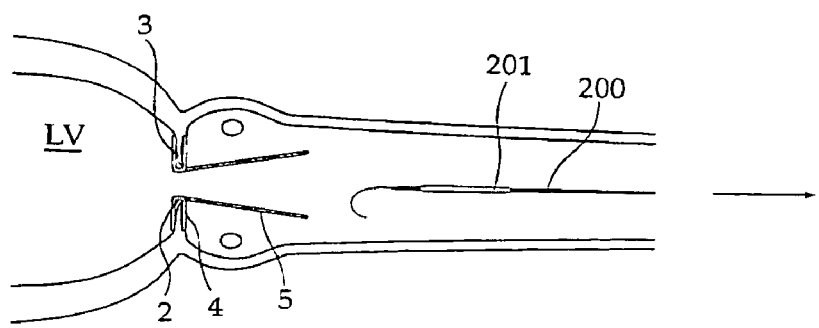

Sheath 202 is then moved to one side (FIG. 15B) to release, for expansion, first annular clamp 3 (FIG. 15C), then annular clamp 4 (FIGS. 15D, 15E), and finally the diverging conical section 5 of the prosthetic device (FIG. 15F). Balloon 201 is then inflated (FIG. 15G) to firmly press the base section 2 within the orifice, and then deflated (FIG. 15H) to permit the catheter 200, together with the balloon 201 and sheath 202, to be removed from the artery, leaving the prosthetic device clamped within the orifice.

Since the prosthetic device is clamped with the orifice by the two annular clamps 3, 4, it may not be essential use a balloon; nonetheless this may be done to better assure proper implantation of the prosthetic device within the orifice. However, the provision of the two annular clamps 3, 4 enables the throat section 2 to be expanded only slightly, i.e., to a much lesser extent than in a conventional stent-type implantation, and thereby reduces the risk of obstructing or occluding the coronary arteries.

Figure 16A:
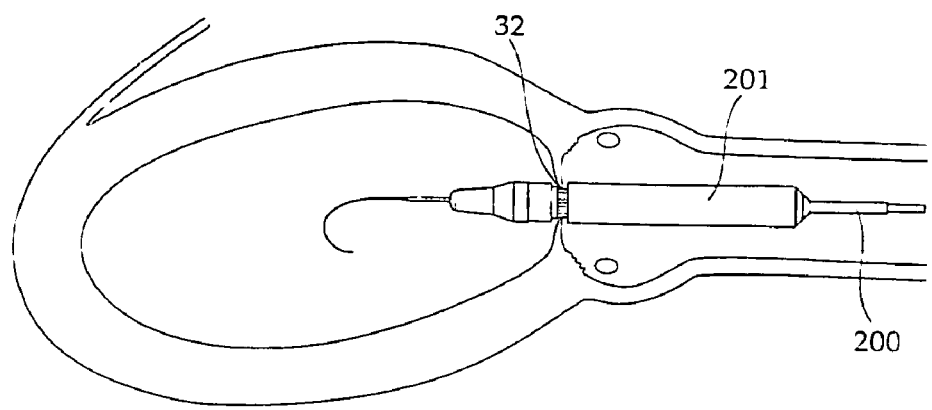
Figure 16B:
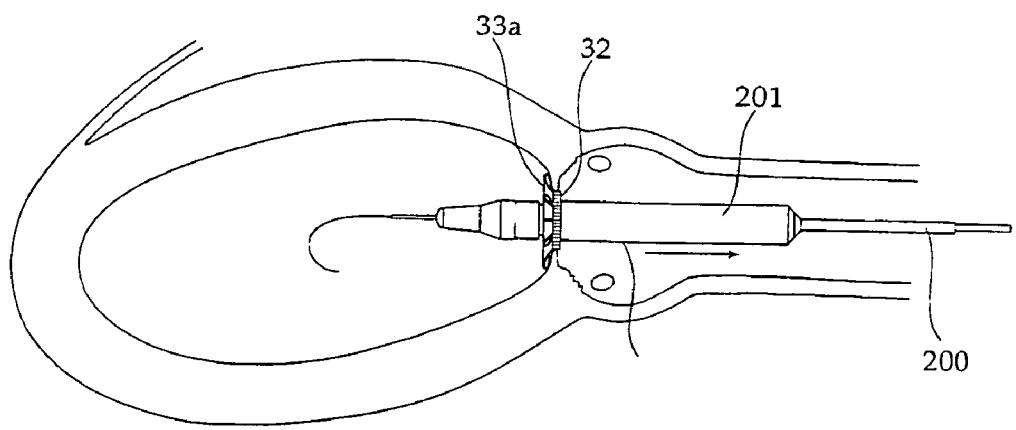
Figure 16C:
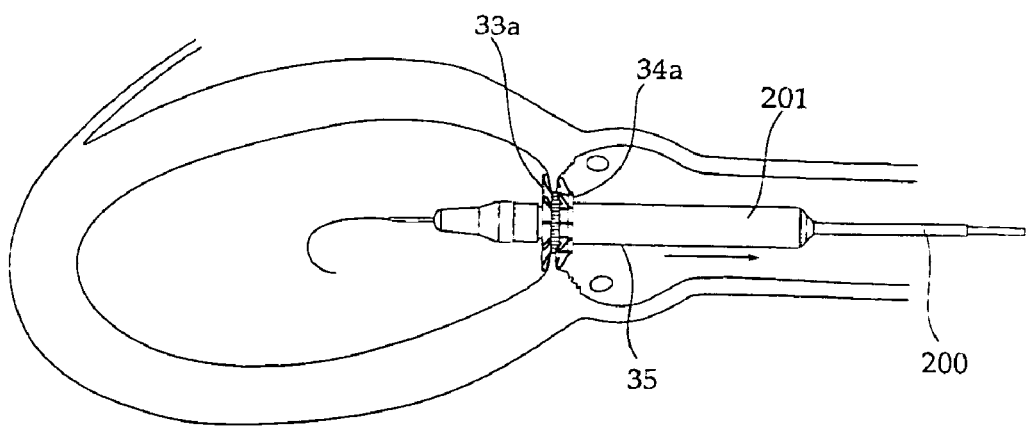
Figure 16D:
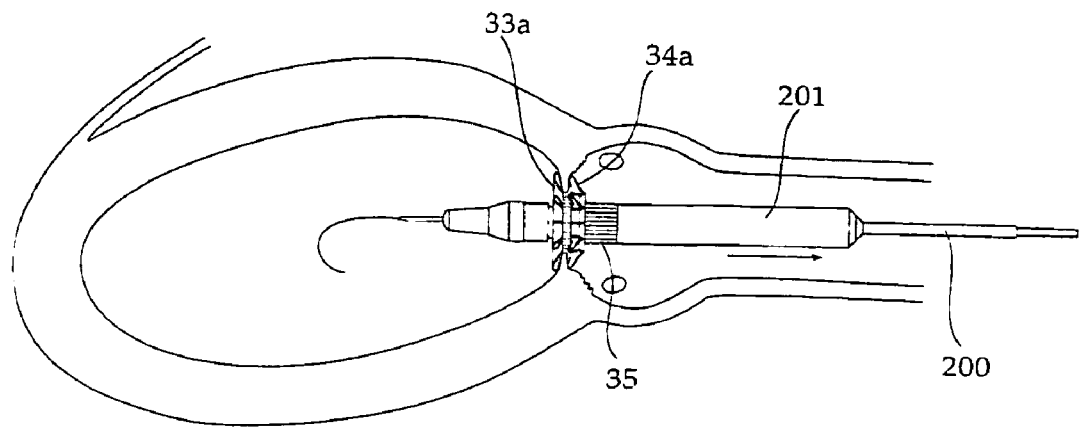
Figure 16E:
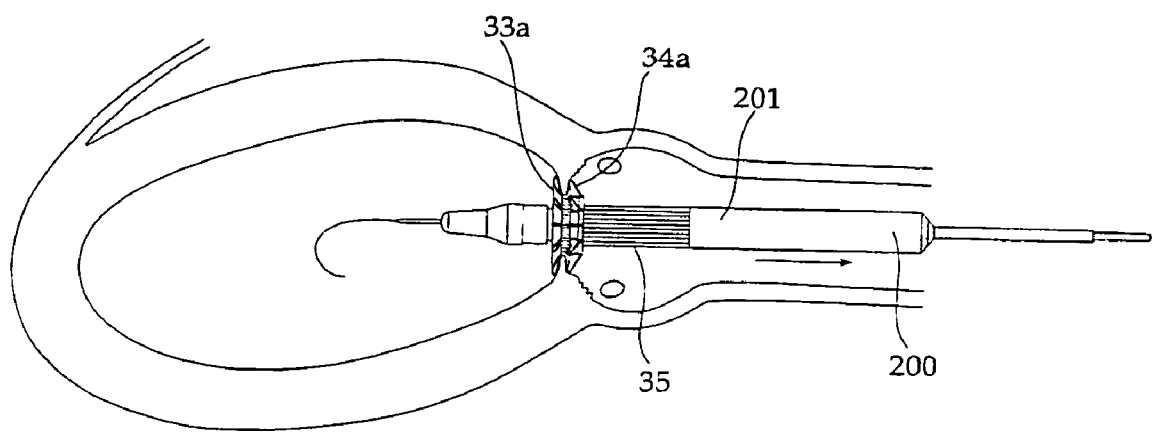
Figure 16F:
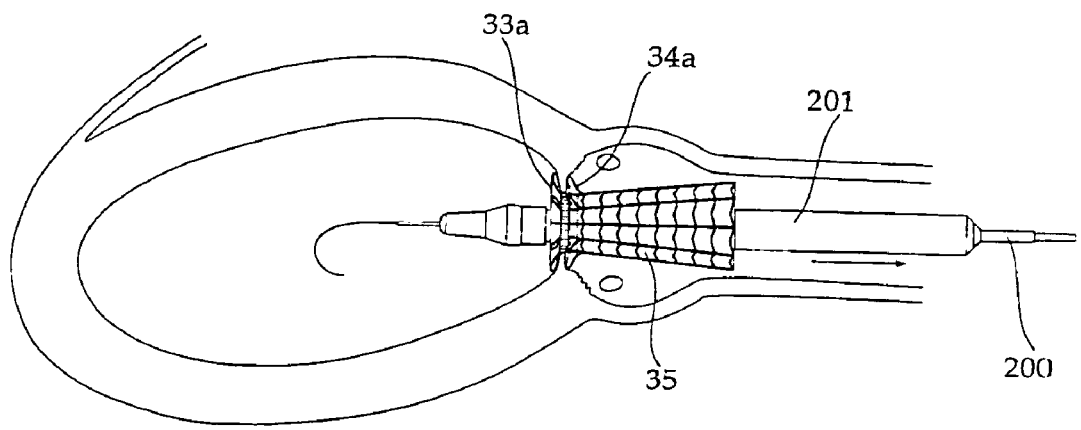

FIGS. 16A–16F illustrate the above-described one-sheath method of deploying the prosthetic device illustrated in FIG. 11 (i.e., including the annular array of bracing elements 40) through the following conditions: FIG. 16A, wherein the throat section 32 is located within the aortic orifice; FIG. 16B, wherein the sheath 201 has been moved to one side sufficient to release the clasping members 33*a* of clamp 33; FIG. 16, wherein continued movement of the sheath releases the clasping members 34*a* of the other annular clamp 34; FIGS. 16D and 16E, wherein continued movement of the sheath starts to release the diverging section 35 of the prosthetic device; and FIG. 16F, wherein the sheath has been moved sufficiently to release for expansion the complete prosthetic device, including the diverging section 35 and the bracing elements 40 around the diverging section 35. As shown particularly in FIG. 16F, the bracing elements 40 may be configured so as not to obstruct the coronary arteries CA in the implanted condition of the prosthetic device.

While the method as illustrated in FIGS. 16A–16*h* does not use an inflatable balloon, it will be appreciated that such an inflatable balloon could also be used, as described above with respect to FIGS. 15A–15H, to better assure firm implantation of the prosthetic device in the aortic orifice.

Two-Sheath Mode of Deployment

FIGS. 17A–17*h* illustrate a two-sheath method of deployment of the prosthetic device. For purposes of example, this prosthetic device is that illustrated as FIGS. 4–8 described below.

In the two-sheath method, the catheter, therein designated 300, includes a first sheath 301 at the outer end to engage annular clamp 13 of the prosthetic device, and a second sheath 302 extending inwardly from sheath 301 so as to engage annular clamp 14 and the diverging conical section 15 of the prosthetic device. This is the condition illustrated in FIG. 17A.

Figure 17A:
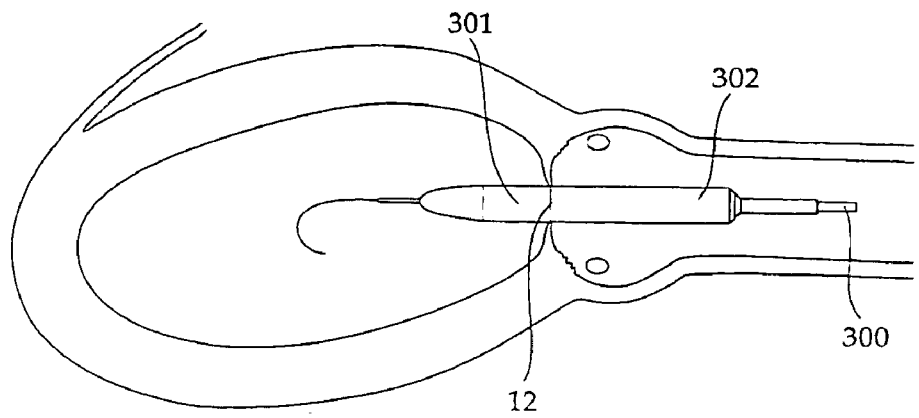
FIGS. 17A–17F illustrate a two-sheath method of implanting a prosthetic device in accordance with the present invention.
Figure 17B:
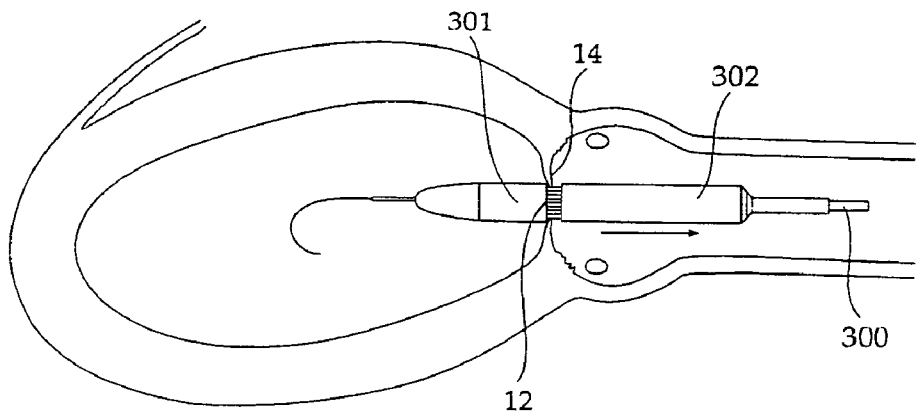
Figure 17C:
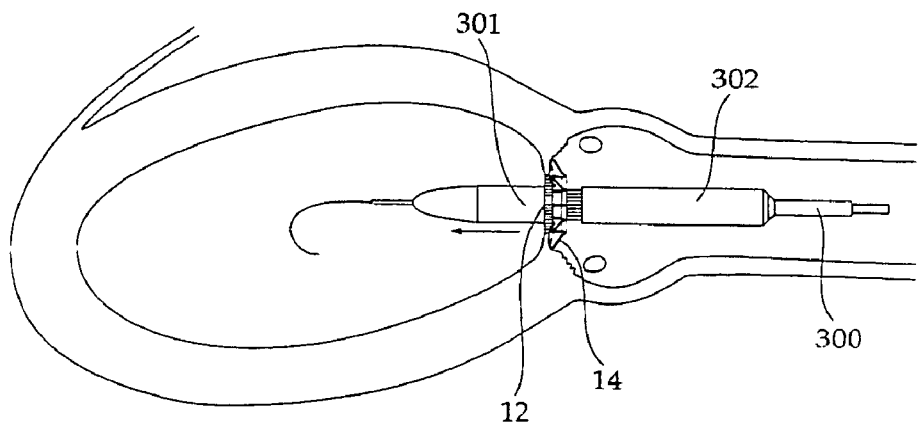

The catheter is first manipulated to locate throat section 12 of the prosthetic device in the aortic orifice (FIG. 17A). Sheath 302 is then moved laterally to one side (rightwardly in the sense of the drawing) in order to release annular clamp 14 (FIG. 17B). When that clamp has been released, the catheter is then moved inwardly of the heart (leftwardly) a slight amount (FIG. 17C) to firmly bring clasping members 14*a* of annular clamp 14 against the respective face of the valve leaflets, such that annular clamp 14 firmly engages the aorta face (18, FIG. 8) of the valve leaflets as shown in FIG. 17C.

Figure 17D:
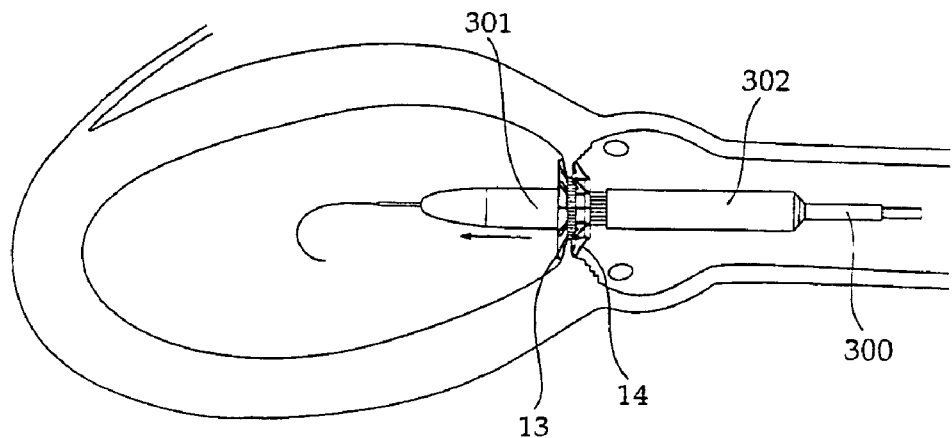

Outer sheath 301 is then moved away from sheath 302, i.e., leftwardly, further into the heart. This releases annular clamp 13 to its expanded state into contact with the surface (19, FIG. 8) of the valve leaflets facing the heart left-ventricle (FIG. 17D). At this time the catheter 300 may then be moved in the opposite direction (rightwardly) to firmly engage clasping members 13*a* of annular clamp 13 with that surface of the valve leaflet.

Figure 17E:
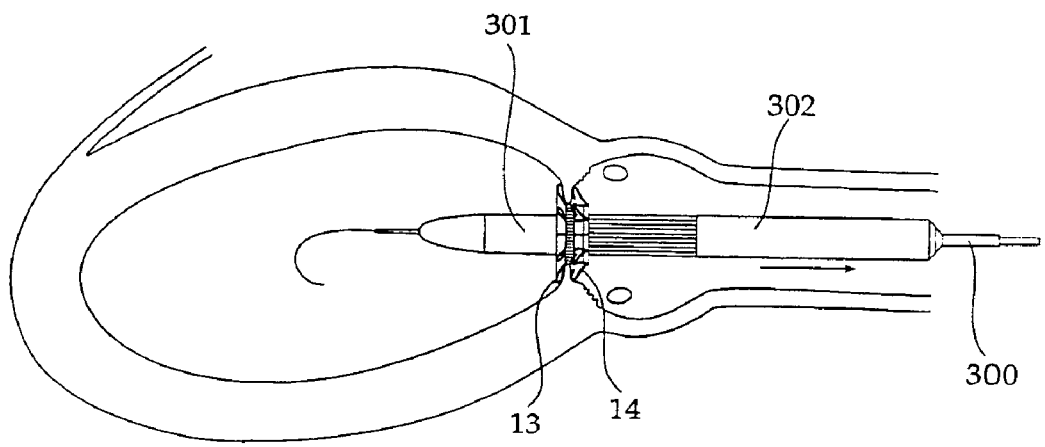
Figure 17F:
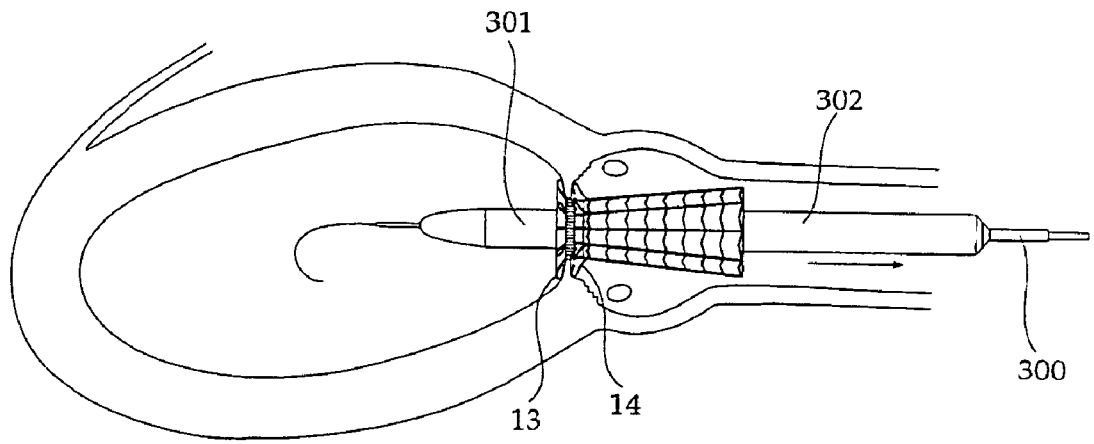

Sheath 302 within the aorta may then be moved further away from sheath 301, to thereby release the remainder of the prosthetic device for expansion, as shown in FIGS. 17E and 17F.

The catheter illustrated in FIGS. 17A–17F may also include a balloon (not shown) if desired, so as to slightly further expand base 12 within the aortic orifice, in which case the balloon would then be deflated in order to permit removal of the catheter and its sheaths.

It will be appreciated that in the above described deployment methods, even if no balloon is used, the base section of the respective prosthetic device will still expand slightly when the respective sheath or sheaths are removed, to firmly seat the base section within the aortic annulus and also to permit removal of the catheter and its sheath or sheaves. However, providing such a balloon permits an additional expansion of the base section of the prosthetic device sufficient to better assure firm implantation within the orifice, but not to the extent of obstructing or occluding the coronary arteries.

Figure 18A:
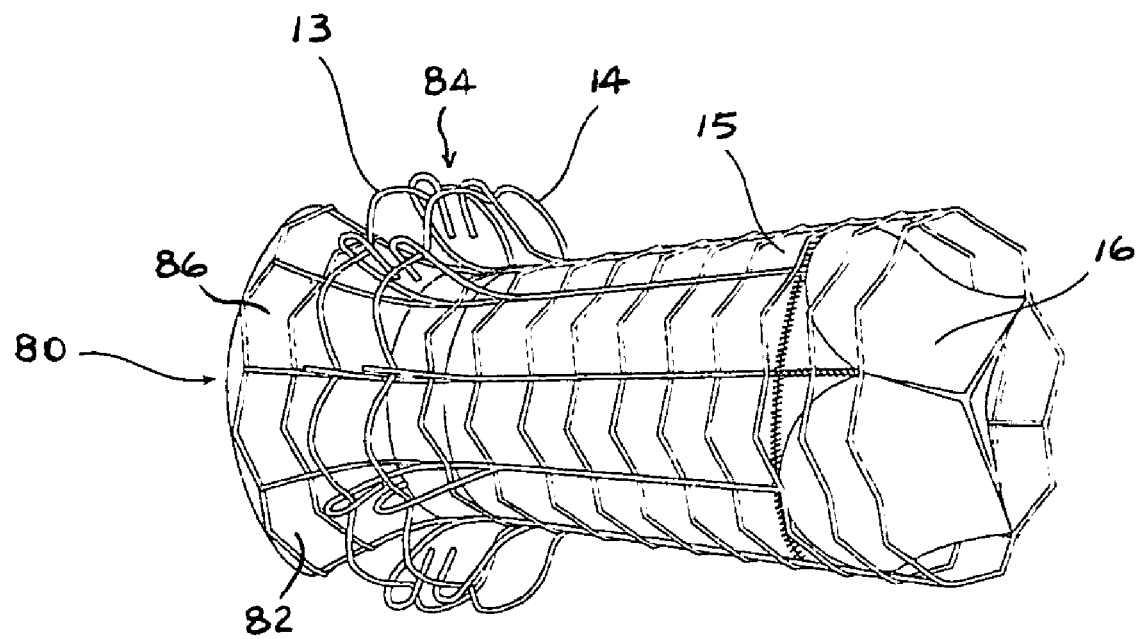
FIGS. 18A and 18B are simplified pictorial and side-view illustrations of a prosthetic device, constructed and operative in accordance with yet another embodiment of the present invention.
Figure 18B:
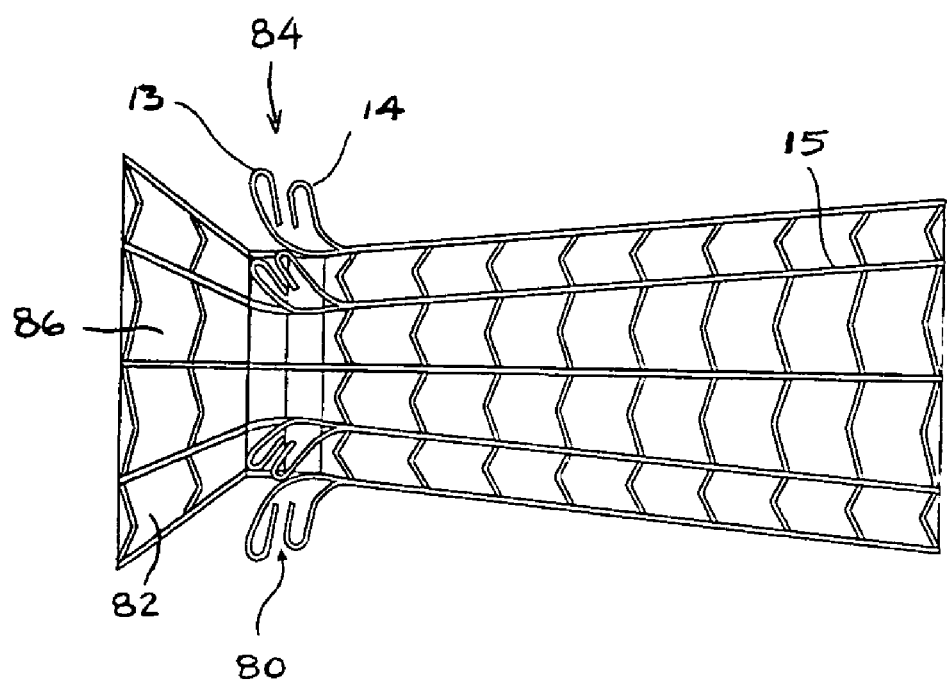

Reference is now made to FIGS. 18A and 18B, which illustrate a prosthetic device 80, constructed and operative in accordance with yet another embodiment of the present invention. Prosthetic device 80 may be constructed similarly to prosthetic device 10 of FIG. 4, with like elements being designated by like numerals. Prosthetic device 80 may include a proximal attachment appliance 82 (on the ventricular or inlet side of the device), which may consist of an array of clasping elements 84 covered by a liner 86 bent in order to extend to and cover the walls which form the left ventricular outflow tract (basal ventricular septum, basal portion of the anterior mitral leaflet). The proximal attachment appliance 82 and liner 86 may have a horn shape with the proximal end of the horn being wider than the distal end of the horn (near the clasping elements 84). This shape may create a ventricular inlet in form of a covered wall stent (or wall-stent like) with radial forces acting to stabilize the device by pressing its inlet against the ventricular septum and the basal anterior leaflet. This inlet may be symmetric, or asymmetric, i.e. extending over a shorter segment of the anterior leaflet, so as not to compromise mitral valve competence.

Figure 19A:
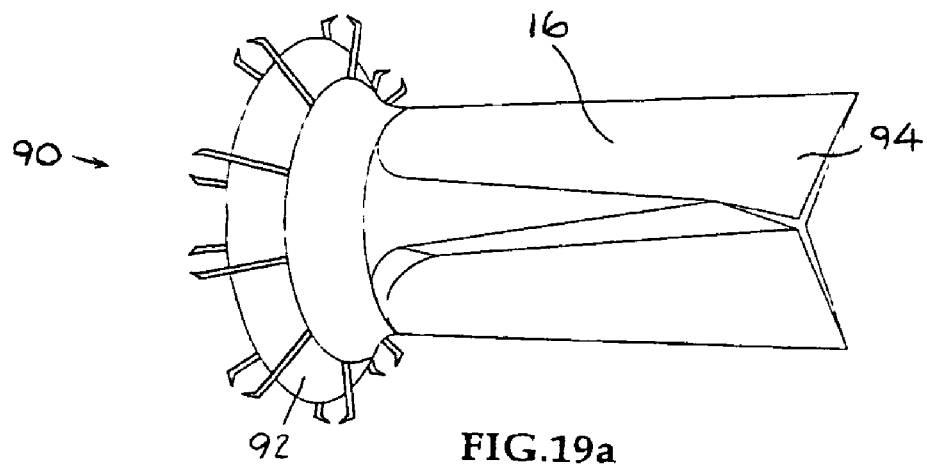
FIGS. 19A and 19B are simplified pictorial and side-view illustrations of a prosthetic device, constructed and operative in accordance with still another embodiment of the present invention, and including a valve of biocompatible material attached to an inlet of relatively small diameter, with a diverging pressure-recovering outlet starting approximately where the fully opened valve cusps end.
Figure 19B:
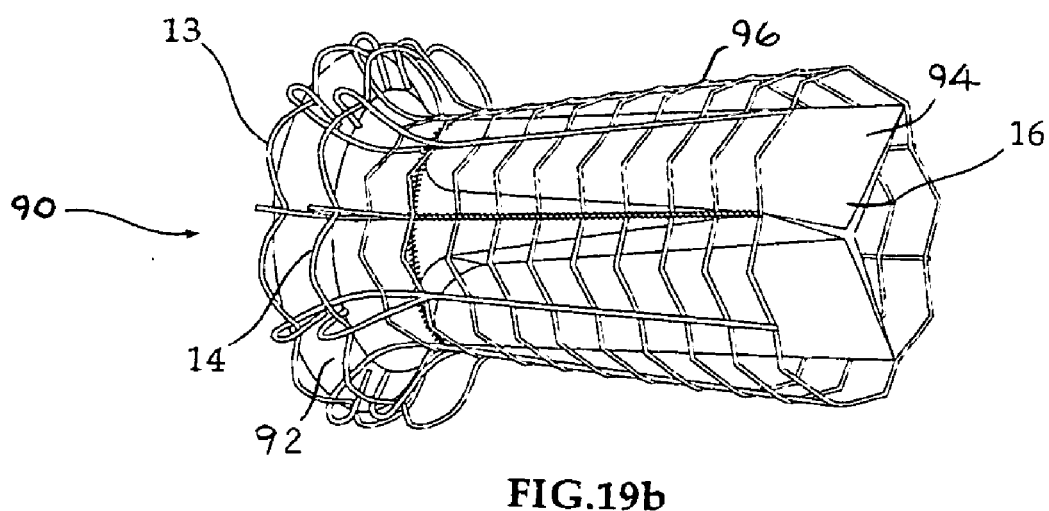
Figure 19C:
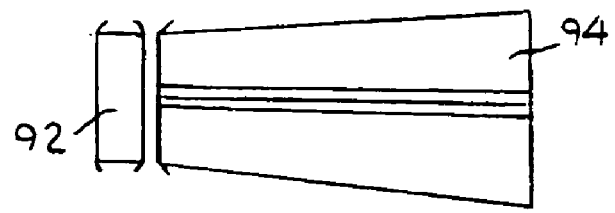
FIG. 19C is a simplified illustration of a variation of the prosthetic device of FIGS. 19A and 19B, in which the diverging outlet is not connected with the prosthesis in order to allow for a two-staged implantation.

Reference is now made to FIGS. 19A and 19B, which illustrate a prosthetic device 90, constructed and operative in accordance with yet another embodiment of the present invention. Prosthetic device 80 may be constructed similarly to prosthetic device 10 of FIG. 4, with like elements being designated by like numerals. In prosthetic device 90, a valve 16 of biocompatible material attached to an inlet 92 of relatively small diameter (typically, but not exclusively 12 to 16 mm), will be implanted into the native valve, with a diverging pressure-recovering outlet 94 starting approximately where the fully opened valve cusps end. Thus, the fully opened valve may in systole form a straight segment (the length of which is given by the valve's cusp) and in continuation of the inlet direct blood flow into the diverging pressure-recovering outlet. In diastole, valve closure will create a space between the valve prosthesis and the diverging outlet, roughly given by the length of the cusps, thus allowing blood supply of the coronaries through the proximal (upstream) end of the diverging outlet. In one embodiment the distal diverging outlet 94 may be connected via ribs, struts, or other connecting structure 96 to the valve prosthesis (e.g., the inlet 92 holding the cusps). In another embodiment, seen in FIG. 19C, the diverging outlet 94 may not be connected with the prosthesis (e.g., not connected to inlet 92) in order to allow for a two-staged implantation (either the diverging outlet first and the prosthesis through the already deployed outlet, or vice versa). In this configuration the diverging outlet may be covered up to its distal (downstream) end that extends to the aortic walls in the manner of a wall-stent, or, the liner may end before the aortic wall is reached, thus allowing for coronary blood supply through a passage between aortic wall and diverging outlet.

In another embodiment the pressure recovering device may be deployed above the native valve, with the native valve left in place. The pressure recovering device may have an internal covered shape which forms a diverging diffuser. The internal shape may have a converging section or a straight section (constant area). It may be placed above the narrowed aortic valve orifice in order to engage the exiting high-velocity jet before kinetic energy dissipation takes place, leading to early reattachment of the streamlines of flow to the liner covering the device. The diverging shape of the device's outlet may then enable gradual expansions of the streamlines of flow, allowing flow velocity to decrease gradually without energy dissipation and kinetic energy to be reconverted into lateral pressure (pressure recovery). The proximal (upstream) end may start above the coronary arteries, preferably, but not exclusively, at the sinotubular junction; in this embodiment coronary blood supply occurs in the same manner, as before the implantation of the device, while the device serves as an aortic endoprosthesis reshaping the lumen of the aorta so as to allow pressure recovery. In another embodiment the proximal (upstream) end of the device starts at or immediately above the native valve in a subcoronary position, while coronary blood flow is provided through the space left between the end of the liner at the distal (downstream) end of the diverging outlet and its attachment to the aortic wall in a wall stent-like manner.

While the invention has been described with respect to several preferred embodiments, it will be appreciated that these are set forth merely for purposes of example, and that many other variations, modifications and applications of the invention may be made.

What is claimed is:

1. A prosthetic device, comprising:
   a valve-orifice attachment member at an upstream end of said prosthetic device, said valve-orifice attachment member configured for attachment to a native valve site of a patient;
   a diverging blood flow pathway, comprising a pathway fluid inlet coupled to said valve-orifice attachment member,
      said pathway configured to flex between an open position thereof and a closed position thereof in response to a cardiac cycle of said patient,
   said diverging blood flow pathway defining a single blood flow field that extends downstream from said pathway fluid inlet,
   said pathway fluid inlet having at its narrowest cross-section a first cross-sectional area for blood flow therethrough,
      said pathway comprising an outlet having a second cross-sectional area at a downstream end of said prosthetic device; and
   a pathway support configured for attachment to said pathway, and that is operative, when attached to said pathway, generally to maintain a diverging configuration of said diverging blood flow pathway,
   wherein, regardless of whether said pathway support is attached to said pathway, said second cross-sectional area is greater than said first cross-sectional area when said pathway is in said open position thereof.

2. The prosthetic device according to claim 1, wherein said diverging blood flow pathway is shaped so as to define a diverging taper that causes fluid to flow therethrough with pressure recovery at said outlet.

3. The prosthetic device according to claim 2, wherein said taper widens with a widening angle $\alpha$ from 0.1° to 50°.

4. The prosthetic device according to claim 2, wherein said taper widens with a widening angle $\alpha$ of approximately 5–8°.

5. The prosthetic device according to claim 1, wherein said diverging blood flow pathway comprises an inner envelope that lines an inner surface thereof.

6. The prosthetic device according to claim 1, comprising a base section to which said valve-orifice attachment member is coupled, wherein said base section is coupled to said pathway fluid inlet and is non-divergent downstream.

7. The prosthetic device according to claim 6, wherein said base section is convergent downstream.

8. The prosthetic device according to claim 1, wherein said valve-orifice attachment member comprises clasping members adapted to clasp opposite sides of a native valve of said native valve site near an orifice of said native valve.

9. The prosthetic device according to claim 1, wherein said valve-orifice attachment member comprises an annular clamp adapted to engage native valve leaflets of said native valve.

10. The prosthetic device according to claim 1, further comprising an annular array of bracing elements at said outlet of said diverging blood flow pathway engageable with an inner surface of a blood vessel of said patient.

11. The prosthetic device according to claim 1, wherein said diverging blood flow pathway is conical.

12. The prosthetic device according to claim 1, wherein said diverging blood flow pathway is curved convexly.

13. The prosthetic device according to claim 1, wherein said diverging blood flow pathway is curved concavely.

14. The prosthetic device according to claim 1, further comprising a plurality of axially-extending struts pivotally mounted near the valve-orifice attachment member and extending through at least a portion of said diverging blood flow pathway.

15. The prosthetic device according to claim 1, wherein said valve-orifice attachment member comprises an inner envelope that lines an inner surface thereof.

16. The prosthetic device according to claim 1,
   wherein said pathway support comprises a plurality of axially-extending struts,
   wherein said diverging blood flow pathway comprises a plurality of portions thereof, each portion disposed between a respective pair of said struts, and
   wherein there is no structural member of said prosthetic device intervening between the portions of said diverging blood flow pathway and blood of said patient within or outside said diverging blood flow pathway, when said valve-orifice attachment member is attached to said valve site.

* * * * *